(12) United States Patent
Freeman et al.

(10) Patent No.: US 7,780,973 B2
(45) Date of Patent: Aug. 24, 2010

(54) METHOD AND DEVICE FOR MINIMALLY INVASIVE IMPLANTATION OF BIOMATERIAL

(75) Inventors: Lynetta Jean Freeman, West Chester, OH (US); Mark W. DiFrancesco, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1516 days.

(21) Appl. No.: 10/736,421

(22) Filed: Dec. 15, 2003

(65) Prior Publication Data
US 2005/0131386 A1 Jun. 16, 2005

(51) Int. Cl.
*A61F 2/02* (2006.01)
(52) U.S. Cl. ........................................ 424/423
(58) Field of Classification Search .................. None
See application file for complete search history.

(56) References Cited

U.S. PATENT DOCUMENTS

| | | | |
|---|---|---|---|
| 4,902,295 A | 2/1990 | Walthall et al. | |
| 4,987,136 A | 1/1991 | Kreek et al. | |
| 5,254,133 A | 10/1993 | Seid | |
| 5,508,397 A | 4/1996 | Or et al. | |
| 5,531,759 A | 7/1996 | Kensey et al. | |
| 5,561,140 A | 10/1996 | Kawai et al. | |
| 5,599,927 A | 2/1997 | Or et al. | |
| 5,604,203 A | 2/1997 | Balasubramaniam | |
| 5,604,293 A | 2/1997 | Fiddes et al. | |
| 5,604,294 A | 2/1997 | Luly et al. | |
| 5,612,350 A | 3/1997 | Or et al. | |
| 5,674,722 A | 10/1997 | Mulligan et al. | |
| 5,798,113 A * | 8/1998 | Dionne et al. | 424/422 |
| 5,859,031 A | 1/1999 | Hamilton et al. | |
| 5,891,462 A | 4/1999 | Carrara | |
| 5,912,227 A | 6/1999 | Croom, Jr. et al. | |
| 5,912,253 A | 6/1999 | Cottens et al. | |
| 5,925,649 A | 7/1999 | Hersperger et al. | |

(Continued)

FOREIGN PATENT DOCUMENTS

WO  WO 2004/084857 A  10/2004

OTHER PUBLICATIONS

Mollinson, et al.; "Discovery of Ascomycin Analogs with Potent Topical but Weak Systemic Activity for Treatment of Inflammatory Skin Diseases"; Current Pharmaceutical Design (1998); pp. 367-380; vol. 4; Bentham Science Publishers B.V.

(Continued)

*Primary Examiner*—Carlos A Azpuru
(74) *Attorney, Agent, or Firm*—Frost Brown Todd LLC

(57) ABSTRACT

A minimally invasive method of placing a delivery device substantially adjacent to vascular tissue and a device for use with such a method are disclosed. The delivery device may be a flexible biological construct with a flexible tethering means. The delivery device may be percutaneously inserted near vascular tissue such as, for example, peritoneal tissue. When the delivery device has been inserted, the tether may be used to pull the delivery device toward the vascular tissue and secure the device thereto. Contact between the front surface of the delivery device and the vascular tissue may be maintained by making and keeping the tether substantially taut. The delivery device may serve accomplish sustained delivery of active agents.

37 Claims, 11 Drawing Sheets

U.S. PATENT DOCUMENTS

| | | | |
|---|---|---|---|
| 5,990,131 | A | 11/1999 | Hamilton et al. |
| 5,994,299 | A | 11/1999 | Barriere et al. |
| 6,004,973 | A | 12/1999 | Guitard et al. |
| 6,007,840 | A | 12/1999 | Hauer et al. |
| 6,171,298 | B1 | 1/2001 | Matsuura et al. |
| 6,179,826 | B1 | 1/2001 | Rebischer et al. |
| 6,235,713 | B1 | 5/2001 | Achen et al. |
| 6,406,498 | B1 | 6/2002 | Törmälä et al. |
| 2003/0021787 | A1 | 1/2003 | Hung et al. |

OTHER PUBLICATIONS

Liu, C.D., et al.; "*A Novel Synthetic Analog of Peptide YY, BIM-43004, Given Intraluminally, Is Proabsorptive*"; Journal of Surgical Research (1995); pp. 80-84; vol. 59; Academic Press, Inc.

Litvak, D.A.; "*Characterization of Two Novel Proabsorptive Peptide YY Analogs, BIM-43073D and BIM-43004C*"; Digestive Diseases and Science (Mar. 1999); pp. 643-648; vol. 44(3); Plenum Publishing Corporation.

King, P.J., et al.; "*Regulation of Neuropeptide Y Release by Neuropeptide Y Receptor Ligands and Calcium Channel Antogonists in Hypothalamic Slices*"; Journal of Neurochemistry (1999); pp. 641-646; vol. 73(2); International Society for Neurochemistry.

Giannis, A., et al.; "*Peptidomimetics in Drug Design*"; Advances in Drug Research (1997); vol. 29(1); Academic Press Limited.

Nabel, E.G., et al.; "*Recombinant Gene Expression in Vivo Within Endothelial Cells of the Arterial Wall*"; Science Reports; Jun. 16, 1989; pp. 1342-1344; vol. 244.

Jeong, S. Y., et al.; "Self-regulating insulin in delivery systems. III. In vivo studies." Journal of Controlled Release, vol. 2/-(143-152). Coden: JCREEC, 1985, XP002322808 *Abstract*.

* cited by examiner

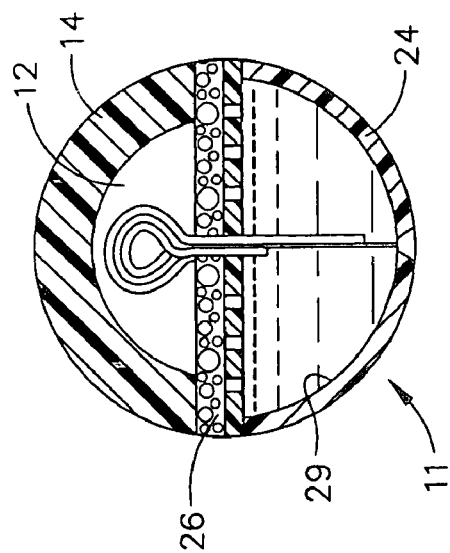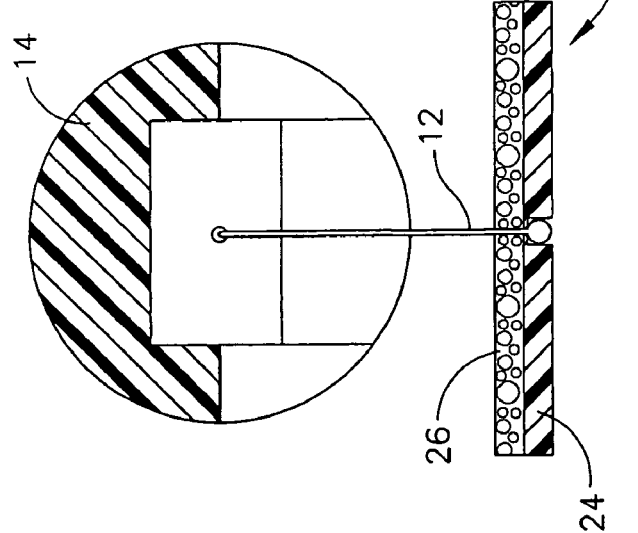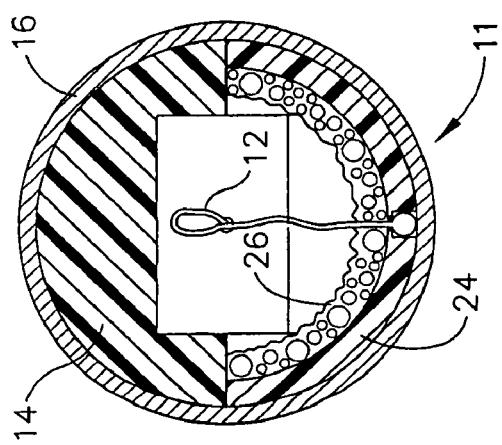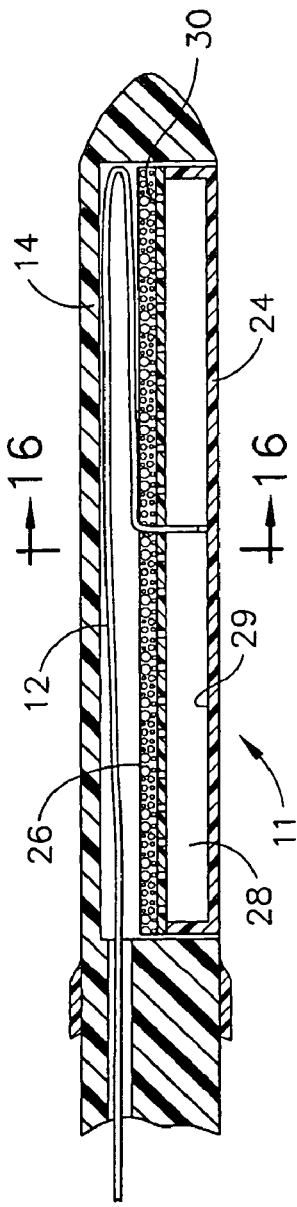
FIG. 16
FIG. 14
FIG. 13
FIG. 15

METHOD AND DEVICE FOR MINIMALLY INVASIVE IMPLANTATION OF BIOMATERIAL

BACKGROUND OF THE INVENTION

The present invention relates generally to the implantation of biomaterial, and is particularly directed to a method and a device that accomplishes the same in a minimally invasive manner. Specifically, the present invention relates to an active agent delivery biomaterial and methods for long-term delivery of a prophylactic or therapeutic agent by implantation of the active agent delivery biomaterial.

Many of the known implantation methods involve the use of a tamping means to drive the implant down a cannula or similar tubular implement into the body. Such tamping involves the use of a pushing tool, such as a rod or wire, which must be inserted into the tubular implement behind the implant to accomplish the tamping. Other possible implantation methods include the extension of a capped second tubular implement down the bore of a first tubular implement inside the body; where the second tubular implement contains the implant and releases the implant when the extension of the second tubular implement reveals an opening in the side of the second tubular implement through which the implant may fall into the body.

The vascular nature of the peritoneal wall is well known in the art. While the art has taught the implantation of materials on or near peritoneal tissue, such teachings have focused on the structural repair or prevention of hernial ruptures. Thus, the art lacks teachings of implantation on or near peritoneal tissue for sustained delivery of materials for non-hernial purposes. While the art has taught the implantation of cell capsules for sustained delivery of neuroactive substances in the central nervous system, such implantation means are relatively inflexible, and their utility is substantially limited to the central nervous system. A relatively inflexible implant would not fully take advantage of the vascular nature of tissue such as peritoneal tissue if implanted on or near such tissue, as a relatively inflexible implant would fail to maximize the surface contact between the implant and the vascular tissue. The maximization of surface-to-surface contact serves to achieve a more efficient, direct exchange of biomaterials between an implant and vascular tissue.

There exists a strong need for the elimination of the undesirable physiological and economic problems associated with long-term drug therapy, while maintaining the advantageous therapeutic properties of the treatment. Due to the risks that certain drugs impose, researchers have developed systems for administering such drugs to aid in the treatment of ailments and diseases. The systems have been designed largely to reduce and to control the release rate of incorporated drugs. However, these systems fail to achieve the surprising and unexpected results obtained by the present invention.

Thus, there exists a need for a minimally invasive method to place and maintain a relatively flexible implant within the body, substantially adjacent to vascular tissue, and an implant device capable of sustained delivery of therapeutic or prophylactic materials or other active agents.

BRIEF SUMMARY OF THE INVENTION

The invention features devices and methods for the delivery of active agents in a subject. The active agent formulation may be stored within an active agent delivery system (e.g., contained in a delivery layer of the system or a reservoir within the controlled active agent delivery system). The active agent formulation may comprise an amount of active agent sufficient for treatment and is stable at body temperatures (e.g., no unacceptable degradation) for the entire preselected treatment period. The active agent delivery systems may store the active agent formulation safely (e.g., without dose dumping), provide sufficient protection from bodily processes to prevent unacceptable degradation of the formulation, and release the active agent formulation in a controlled fashion at a therapeutically effective rate to the subject. In use, the active agent delivery system may be implanted in the subject's body at an implantation site, and the active agent formulation may be released from the active agent delivery system to a delivery site within, for example, the peritoneal or abdominal wall. Once released at the delivery site, the active agent formulation may enter the subject through vascularized tissue.

The present invention may allow a patient greater flexibility of lifestyle, freedom of movement, and the ability to carry out physical activity in a more natural and comfortable manner. The present invention may eliminate the need for frequent injections and the pain associated with multiple daily needle injections, skin irritation, mental anguish suffered by patients having difficulty controlling or maintaining the physiologic parameters pertaining to their clinical condition.

In one embodiment, the invention comprises an active agent delivery device comprising a tethered delivery device and a minimally invasive method of placing such an active agent delivery device substantially adjacent to vascular tissue. The implantation of such a device may provide a sustained delivery of therapeutic, prophylactic, and/or many other types of materials. Generally, the active agent delivery device may be placed within, for example, the abdominal space, within the omentum, within the peritoneal cavity, a space formed when the parietal and visceral layers of the peritoneum, or between the parietal peritoneum and abdominal wall. Other suitable locations for placement are possible.

Contemplated implantation techniques include an approach that positions the active agent delivery device within the peritoneal space through the use of a puncture wound. It may be desirable to use surgical techniques that allow access to the peritoneal cavity, where a small wound exposes the cavity. Following dissection of the peritoneum, an active agent delivery device, as described herein, may be inserted into the space. After allowing for a certain degree of positioning, if necessary, the wound may be closed.

The active agent delivery device may include a biological construct and a tethering means. The delivery device may be substantially flexible and/or have an adhesive front. The tethering means may be made of a substantially flexible material capable of anchoring the delivery device in substantial planar contact with the vascularized tissue. The delivery device may be percutaneously inserted near vascular tissue such as, for example, peritoneal tissue. When the delivery device has been inserted, the tethering means may be used to pull the delivery device toward the vascular tissue, such that the active agent delivery top surface of the delivery device comes in contact with the vascular tissue. Contact between the active agent delivery surface of the delivery device and the vascular tissue may be maintained by making and keeping a tethering means substantially taut. In an alternate embodiment, an adhesive on the active agent delivery surface of the delivery device capable of substantially adhering to the vascular tissue may be used to keep the delivery device substantially in contact with the vascularized tissue.

Any generally tubular or similar implement may be used to insert and/or deploy the delivery device. The insertion implement may be comprised of an inner and an outer tube, where the delivery device is placed within the inner tube. The side of the inner tube may have an opening in which the delivery device may be placed when the inner tube is extended out of the outer tube. Where one end of the delivery device tethering means is attached to the delivery device, the other end of the tethering means may be attached inside the closed distal end of the inner tube. The inner tube may be retracted into the outer tube prior to implantation. After a trocar is inserted into the subject, with the insertion implement positioned within the cannula of the trocar, the inner tube may be extended into the body of the subject. When the extension of the inner tube results in the exposure of the opening in the side of the inner tube to the body cavity, the delivery device may be deployed into the body of the subject. After the delivery device is deployed, the inner tube may again be substantially retracted into the outer tube, without severing the tethering means. Then the trocar may be withdrawn from the body, along with the insertion implement. After the distal end of the insertion implement has been withdrawn, the tether may be seen and manipulated. The tethering means may be severed from the insertion implement and manipulated to hold the delivery device in place.

The present inventors have discovered a device that is suitable for the controlled and sustained release of an agent effective in obtaining a desired local or systemic physiological or pharmacological effect. The device includes an implantable active agent delivery system comprising an effective amount of at least one active agent that, once implanted, the device may give a continuous supply of the agent or agents to internal regions of the body without requiring additional invasive penetrations into these regions. Instead, the device may remain in the body and serve as a continuous source of the agent or agents. The device according to the present invention permits prolonged constant release of active agents over a specific period of months (e.g., 1 month, 2 months, 3 months, 6 months) or years (e.g., 1 year, 5 years, 10 years, 20 years) until the agent is substantially used up.

The types of substances that may be delivered through the delivery device may include drugs (thrombolytics, platelet inhibitors, anti-restenotic agents, beta blockers, ion channel antagonists, positive or negative ionotropic agents, anti-arrhythmics, antibiotics, analgesics, chemotherapeutic agents, other anti-neoplastic agents, etc.), natural or recombinant proteins (e.g., angiogenic proteins such as vascular endothelial growth factor (VEGF), fibroblast growth factors (FGF), epidermal growth factor (EGF), platelet-derived growth factor (PDGF) nerve cell growth factor (NGF) or hepatocyte growth factor (HGF)), cells or cellular preparations (e.g., stem cells, other progenetor cells, myocytes, myoblasts, pancreatic islet cells, dopamine secreting cells, etc.), genes or gene therapy preparations (e.g., viral vectors containing genes for gene therapy applications, genetic material for electrophoretic transmission into cells, plasmids, viral vectors, genetically modified cells, naked DNA, etc.), contrast media or dyes for imaging, radio-labeled diagnostic materials or drugs or other traceable substances, mixtures of any of the above, alone, in solution or in combination with any delivery substance or matrix (e.g., polymer matrices used to inhibit or slow distribution or dissemination of a substance away from its original injection site), dialysis solutions or micro-dialysis solutions, and/or any other type of substances or combinations thereof that may be introduced through the delivery device for any therapeutic, imaging, diagnostic or other purpose.

In various aspects, the active agent may be delivered at a low dose rate, e.g., up to about 0.01 microgram/hr, 0.10 microgram/hr, 0.25 microgram/hr, 1 microgram/hr, or 5, 10, 25, 50, 75, 100, 150, or generally up to about 200 microgram/hr. Specific ranges of amount of active agent delivered may vary depending upon, for example, the potency. In one exemplary embodiment, a drug formulation is delivered at a low volume rate e.g., a volume rate of from about 0.01 microliters/day to about 2 ml/day. Delivery of a formulation may be substantially continuous or pulsate, and may be for a preselected administration period ranging from several hours to years.

In another embodiment, the formulation is delivered at a volume rate of from about 1 ml per day to about 150 ml per day. In another embodiment, the delivering of the formulation is substantially continuous.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Throughout this document, all temperatures are given in degrees Celsius, and all percentages are weight percentages unless otherwise stated. The following are definitions of terms used in this specification. The initial definition provided for a group or term herein applies to that group or term throughout the present specification, individually or as part of another group, unless otherwise indicated.

Unless defined otherwise, all technical and scientific terms used herein have the same meaning as commonly understood to one of ordinary skill in the art to which this invention belongs. Although any methods, devices and materials similar or equivalent to those described herein may be used in the practice or testing of the invention, the preferred methods, devices and materials are now described.

All publications mentioned herein are incorporated herein by reference for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 13 depicts an embodiment of the delivery device with a flexible substrate describing an arc at the outer diameter of the inner tube of the insertion implement.

FIG. 14 is the delivery device of FIG. 13 deployed and assuming a substantially flat shape according to an embodiment of the invention.

FIG. 15 is a cross-section of an embodiment where the delivery device has a reservoir.

FIG. 16 is a cross-section of the embodiment of FIG. 15.

Figure 1:
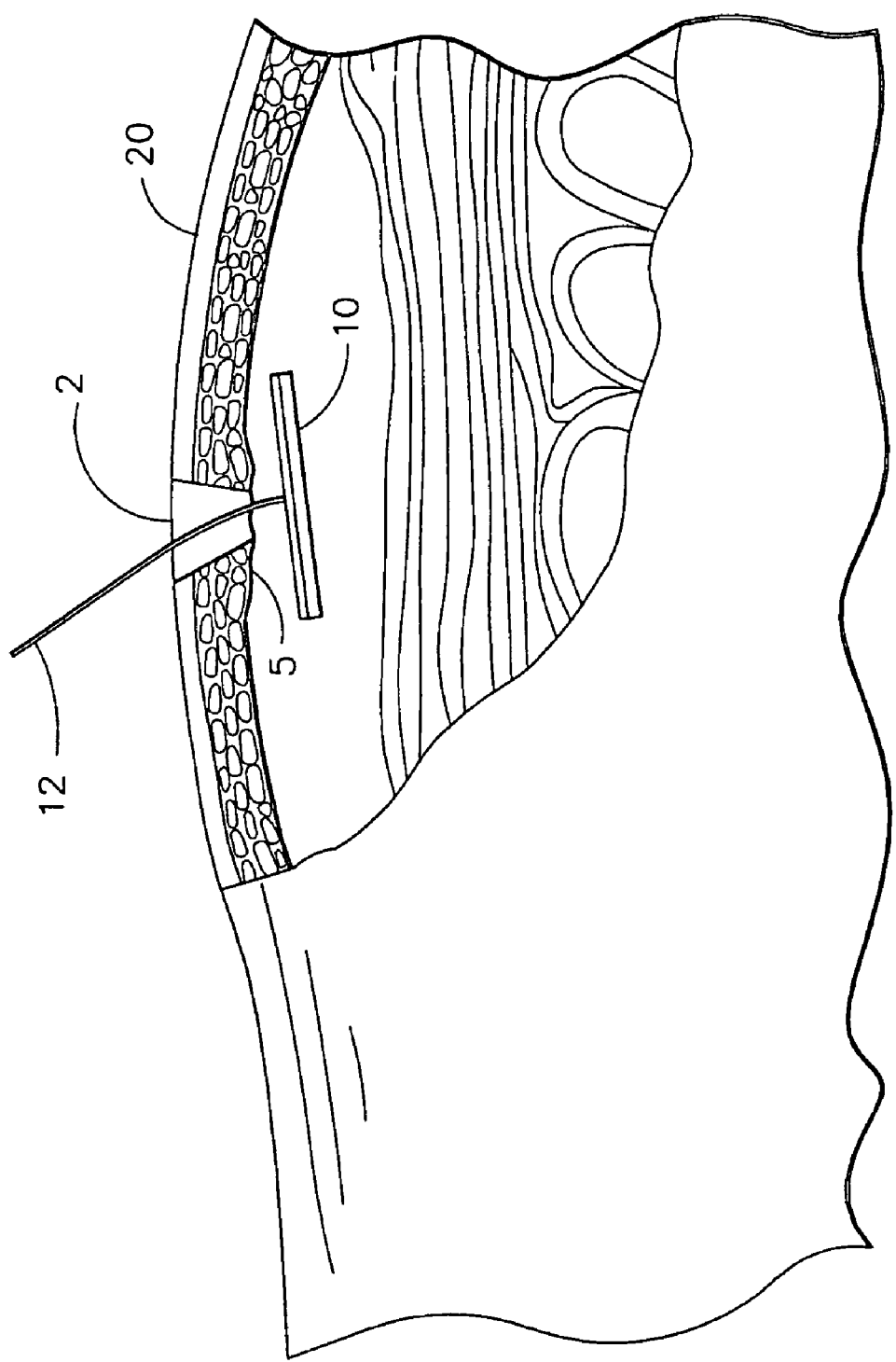
FIG. 1 is a view of a delivery device within an abdomen according to an embodiment of the invention.

Reference will now be made in detail to the present preferred embodiment of the invention, an example of which is illustrated in the accompanying drawings. Alternate embodiments will also be discussed.

DETAILED DESCRIPTION OF THE INVENTION

Before the present method of making transdermal, transmucosal, and/or other delivery devices is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims.

It must be noted that, as used in this specification and the appended claims, the singular forms "a," "an," and "the" include plural referents unless the content clearly dictates otherwise. Thus, for example, reference to a laminated structure containing "a drug" includes a mixture of two or more drugs, reference to "an adhesive" includes reference to two or more of such adhesives, and reference to "an enhancer" includes reference to a mixture of two or more enhancers.

In describing and claiming the present invention, the following terminology will be used in accordance with the definitions set out below.

As used herein, the term, "active agent" includes, without limitation, any substance that it is desired to incorporate into the delivery system of the present invention for sustained or controlled delivery and/or release. An active agent may be in any state, including liquids, solutions, pastes, solids, and the like. The active agent may be a pharmaceutically active agent, such as an active agent and/or diagnostic substance for human or veterinary use. Generally, "active agents" refer, without limitation, to any composition that may be used to the benefit of a mammalian species. Such agents may take the form of ions, macromolecule, small organic molecules, peptides, proteins or polypeptides, oligonucleotides, and oligosaccharides, for example.

The term "active agent delivery device" means an implantable device capable of delivering a therapeutically effective amount of an active agent from a biomaterial and includes a device comprising an implantable device including a tether. The term "active agent delivery device" may be used interchangeably with the term "implant device" or "implant."

As used herein, the term "active gel," "gelled drug," "drug in gel form," and the like includes a drug in which a gelling agent is dispersed to obtain selected flow and surface tension properties for application to laminated patches. Thus, active gel is a liquid drug in a viscous yet flowable state, and may be a colloidal/biphasic or dissolved mixture of liquid drug and a gelling agent. Liquid drug means either a drug that is itself a liquid or is dissolved, suspended, or dispersed in a selected solvent or vehicle. Such a solvent could be a liquid, such as ethanol, water, and the like, or a low-viscosity semi-solid that may be extruded, such as low molecular weight polymers, waxes, petroleum jelly, and the like. Active gel may also include enhancers that may be added to the formulation to facilitate transport of the drug into the body. Active gel may also include a combination of drugs, gelling agents, enhancers, preservatives, antioxidants, anti-irritants, solubilization agents, and the like. The term "gel" is meant to apply to the functional nature of the thickened drug component whether or not the technical definition of a gel is met.

The term "administer" is intended to include introducing the delivery system or device of the present invention into a subject. When administration is for the purpose of treatment, administration may be for either prophylactic or therapeutic purposes. When provided prophylactically, the substance is provided in advance of any symptom. The prophylactic administration of the substance may serve to prevent or attenuate any subsequent symptom. When provided therapeutically, the substance is provided at (or shortly after) the onset of a symptom. The therapeutic administration of this substance may serve to attenuate any actual symptom.

As used herein, the term "biomaterial" includes biocompatible material comprising one or more active agents in a form suitable for delivery within a subject in a therapeutically acceptable amount.

"Delivery enhancement, "penetration enhancement" or "permeation enhancement" as used herein relates to an increase in amount and/or rate of delivery of a compound that is delivered into and across one or more layers of an epithelial or endothelial tissue. An enhancement of delivery can be observed by measuring the rate and/or amount of the compound that passes through one or more layers of animal or human tissue. Delivery enhancement also can involve an increase in the depth into the tissue to which the compound is delivered, and/or the extent of delivery to one or more cell types of the epithelial or other tissue. Such measurements are readily obtained by, for example, using a diffusion cell apparatus as described in U.S. Pat. No. 5,891,462.

"Delivery site" as used herein is meant to include an area of the body to which active agent is delivered for entry into the systemic circulation, e.g., a site which allows systemic access of active agent delivered to the site. Exemplary delivery sites compatible with systemic delivery of active agent include, but are not necessarily limited to, peritoneum and omentum sites. The delivery may be trans-epithelial or through epithelial tissue. An "epithelial tissue" is the basic tissue that covers surface areas of the surface, spaces, and cavities of the body. Epithelial tissues are composed primarily of epithelial cells that are attached to one another and rest on an extracellular matrix (basement membrane) that is typically produced by the cells.

As used herein, the term "drug" or "active agent" or any other similar term means any chemical or biological material or compound suitable for administration by the methods taught in the present invention, that induces a desired biological or pharmacological effect, which may include but is not limited to (1) affecting living processes, (2) having a prophylactic effect on the organism and preventing an undesired biological effect such as preventing an infection, (3) alleviating a condition caused by a disease, for example, alleviating pain or inflammation caused as a result of disease, and/or (4) either alleviating, reducing, or completely eliminating the disease from the organism. The effect may be local, such as providing for a local anaesthetic effect, or it may be systemic. This invention is not drawn to novel drugs or to new classes of active agents. Rather it is limited to devices and methods of making the devices for delivery of drugs or agents that exist in the art or that may later be established as active drugs or agents and that are suitable for delivery by the present invention. Such substances include broad classes of compounds normally delivered into the body, including through body surfaces and membranes. In general, this includes but is not limited to: anti-infectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; tranquilizers; and nicotine and acid addition salts thereof.

Changing either the resistance (the diffusion coefficient) or the driving force (the gradient for diffusion) may increase the flux of a drug across the vascular tissue. Flux may be enhanced by the use of so-called penetration or chemical enhancers. Chemical enhancers are comprised of two primary categories of components, i.e., cell-envelope disordering compounds and solvents or binary systems containing both cell-envelope disordering compounds and solvents.

The term "formulation" means any drug together with a pharmaceutically acceptable excipient or carrier such as a solvent such as water, phosphate buffered saline or other acceptable substance. A formulation may include one or more active agents, and also encompass one or more carrier materials, as known in the art.

The term "implantation site" is used to refer to a site on or in the body of a subject at which an active agent delivery device may be introduced. This includes but is not limited to a puncture or opening in the epidermis through which a delivery device may be inserted. An "implantation site" may be generally proximate to a "delivery site." For example, an "implantation site" may refer to an opening in the outer surface of a subject, while the "delivery site" refers to an area generally contiguous or proximate to the opening on an inner surface of the subject.

The term "macromolecule" as used herein refers to large molecules (MW greater than 1000 daltons) exemplified by, but not limited to, peptides, proteins, oligonucleotides and polynucleotides of biological or synthetic origin. "Small organic molecule" refers to a carbon-containing agent having a molecular weight (MW) of less than or equal to 1000 daltons. The term "peptide" as used herein refers to a compound made up of a single chain of D- or L-amino acids or a mixture of D- and L-amino acids joined by peptide bonds. Generally, peptides contain at least two amino acid residues and are less than about 50 amino acids in length. The term "protein" as used herein refers to a com-pound that is composed of linearly arranged amino acids linked by peptide bonds, but in contrast to peptides, has a well-defined conformation. Proteins, as opposed to peptides, generally consist of chains of 50 or more amino acids. "Polypeptide" as used herein refers to a polymer of at least two amino acid residues and which contains one or more peptide bonds. "Polypeptide" encompasses peptides and proteins, regardless of whether the polypeptide has a well-defined conformation.

"Patterned" or "temporal" as used in the context of active agent delivery is meant delivery of active agent in a pattern, generally a substantially regular pattern, over a pre-selected period of time (e.g., other than a period associated with, for example a bolus injection). "Patterned" or "temporal" active agent delivery is meant to encompass delivery of active agent at an increasing, decreasing, substantially constant, or pulsatile, rate or range of rates (e.g., amount of active agent per unit time, or volume of active agent formulation for a unit time), and further encompasses delivery that is continuous or substantially continuous, or chronic. By "substantially continuous" as used in, for example, the context of "substantially continuous infusion" or "substantially continuous delivery" is meant to refer to delivery of active agent in a manner that is substantially uninterrupted for a pre-selected period of active agent delivery (other than a period associated with, for example, a bolus injection). Furthermore, "substantially continuous" active agent delivery may also encompass delivery of active agent at a substantially constant, pre-selected rate or range of rates (e.g., amount of active agent per unit time, or volume of active agent formulation for a unit time) that is substantially uninterrupted for a pre-selected period of active agent delivery.

The term "substrate" as used herein is meant to include a bottom layer of the active agent delivery device. The substrate may provide mere structural backing and/or may serve one or more other functions. For example, the substrate may include other agents operable to serve the subject and/or the active agent and/or the material containing the active agent. The use of the term "substrate" should not be read as limiting the invention to a delivery device comprising a plurality of layers, for the delivery device may comprise a single layer.

The terms "subject," "individual," and "patient," used interchangeably herein, refer to any subject, generally, by way of example only, a mammal (e.g., human, canine, feline, equine, bovine, ursine, icthiine, porcine, ungulate etc.), to which a active agent may be delivered.

As used herein, the terms, "sustained release" and "controlled release" indicate a prolongation of the duration of release and/or duration of action of an active agent and are well understood in the art and are intended to be interchangeable, unless otherwise indicated. Sustained release, for example, may be for a period of at least 12 hours, at least 24 hours, at least two weeks, at least a month, at least three months, or longer.

The term "systemic delivery" is meant to encompass all parenteral routes of delivery which permit active agent to enter into the systemic circulation, e.g., intravenous, intra-arterial, intramuscular, subcutaneous, intra-adipose tissue, intra-lymphatic, etc.

The term "therapeutically effective amount" is meant an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art.

As used herein, the term "biocompatible" includes any material that is compatible with living tissue or a living system by not being toxic or injurious and not causing immunological rejection. "Biocompatibility" includes the tendency of a material to be biocompatible. As used herein, the term "biocompatible" refers collectively to both the intact delivery device and its contents. Specifically, it refers to the capability of the implanted intact delivery device and its contents to avoid detrimental effects of the body's various protective systems and remain functional for a significant period of time. In addition to the avoidance of protective responses from the immune system, or foreign body fibrotic response, "biocompatible" also implies that no specific undesirable cytotoxic or systemic effects are caused by the delivery device and its contents such as would interfere with the desired functioning of the delivery device or its contents. The biocompatibility of the device is produced by a combination of factors.

Important for biocompatibility and continued functionality are delivery device morphology, hydrophobicity and the absence of undesirable substances either on the surface of, or leachable from, the delivery device itself. Thus, brush surfaces, folds, interlayers or other shapes or structures eliciting a foreign body response are avoided. The delivery device-forming materials are sufficiently pure that unwanted substances do not leach out from the delivery device materials themselves. Additionally, following delivery device preparation, the treatment of the external surface of the delivery device with fluids or materials (e.g. serum) which may adhere to or be absorbed by the delivery device and subsequently impair delivery device biocompatibility are avoided.

First, the materials used to form the delivery device are substances selected based upon their ability to be compatible with, and accepted by, the tissues of the recipient of the implanted delivery device. Substances are used which are not harmful to the recipient or to the isolated biologically active agent. Second, substances used in preparing the biocompatible delivery device are either free of leachable pyrogenic or otherwise harmful, irritating, or immunogenic substances or are exhaustively purified to remove such harmful substances. Thereafter, and throughout the manufacture and maintenance of the delivery device prior to implantation, great care is taken to prevent the adulteration or contamination of the delivery device with substances which would adversely affect its biocompatibility. Third, the exterior configuration of the delivery device, including its texture, is formed in such a manner that it provides an optimal interface with the tissues of the recipient after implantation. This parameter will be defined in part by the site of implantation. For example, if the delivery device will reside in the peritoneal cavity of the recipient, its surface should be smooth. However, if it will be embedded in the soft tissues of the recipient, its surface can be moderately rough or stippled. A determining factor will be whether it is desirable to allow cells of the recipient to attach to the external surface of the delivery device or if such attachment must be avoided. An open-textured or sponge-like surface may promote the ingrowth of capillary beds, whereas a smooth surface may discourage excessive overgrowth by fibroblasts. Excessive overgrowth by fibroblasts is to be avoided, except where capillary undergrowth has occurred, as it may result in the deposition of a poorly-permeable basement membrane around the delivery device and walling off of the isolated cells from contact with the recipient's body.

Certain delivery device geometries have also been found to specifically elicit foreign body fibrotic responses and should be avoided. Thus delivery devices should not contain structures having interlayers such as brush surfaces or folds. In general, opposing delivery device surfaces or edges either from the same or adjacent delivery devices should be at least 1 mm apart, preferably greater than 2 mm and most preferably greater than 5 mm. Preferred embodiments include cylinders, "U"-shaped cylinders, and flat sheets or sandwiches. The surrounding or peripheral region (jacket) of the biocompatible delivery device can optionally include substances which decrease or deter local inflammatory response to the implanted delivery device, and/or generate or foster a suitable local environment for the implanted cells or tissues.

As used herein, the term "bioabsorbable" includes the ability of a material to eventually be absorbed by the body. Preferably, this absorption occurs without adverse effects upon the body.

As used herein, the term "shape memory" includes the ability of a material to return to a preformed shape.

Figure 3:
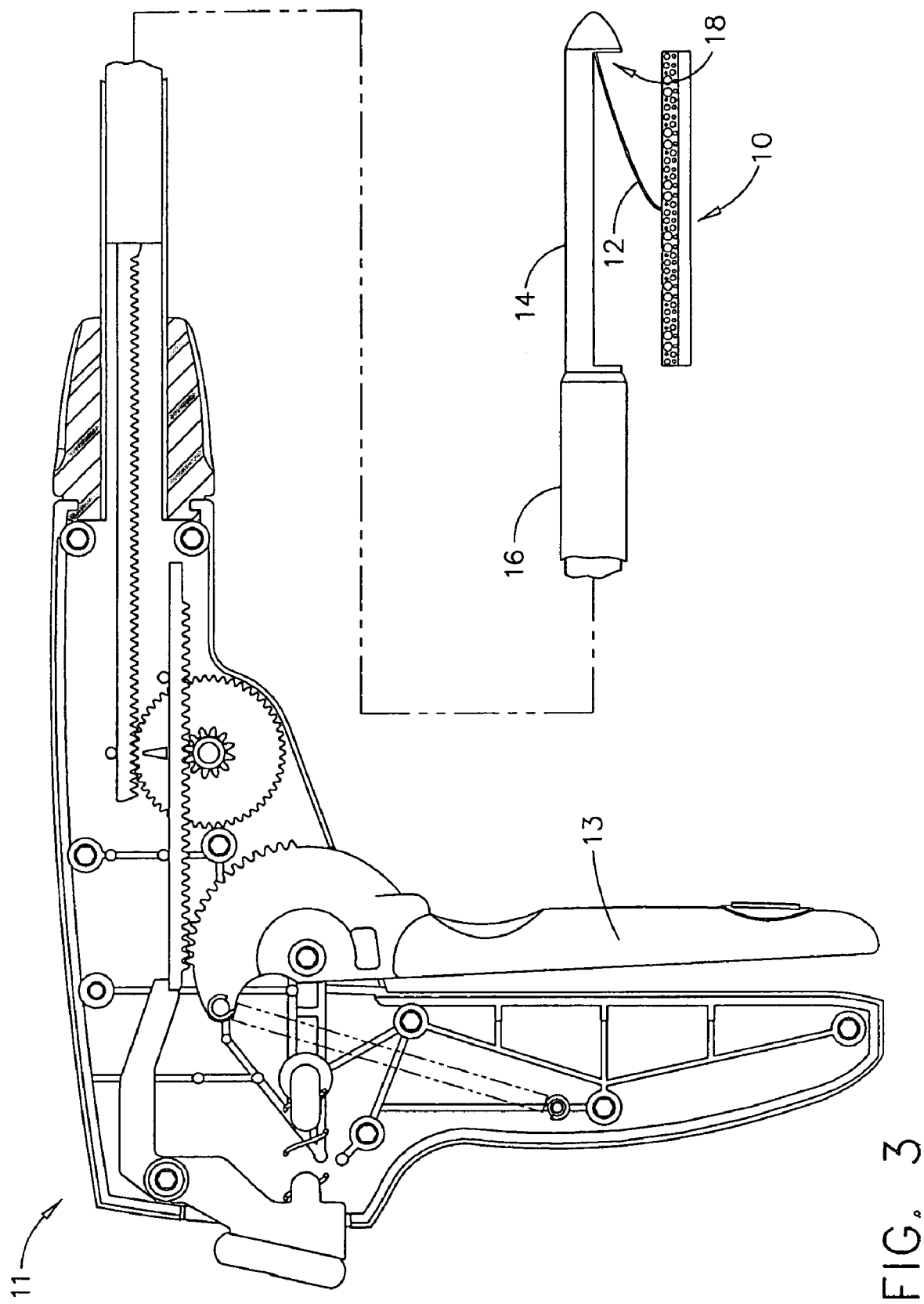
FIG. 3 is a view of an insertion implement with a delivery device according to an embodiment of the invention.

Referring now to the drawings in detail, wherein like numerals indicate the same elements throughout the views, FIG. 3 shows an insertion implement 11 operable to implant an object into the body. The delivery device 10 may be a cell or tissue matrix such as that disclosed in U.S. Pat. No. 4,902,295 by Walthall et al., or any other biomaterial capable of delivering a drug or other therapeutic, prophylactic, or other material. The delivery device 10 may be suspendable from a tether 12, which may be attached to an inner tube 14. The tether 12 should not adversely affect the functioning of the delivery device 10 or the biocompatibility of the delivery device 10.

The insertion implement 11 includes an inner tube 14 and an outer tube 16. The inner tube 14 has a portion removed, creating a cavity 18 to receive the delivery device 10. The inner tube 14 is slidable through the outer tube 16. The outside distal tip of the inner tube 14 may be blunt, rounded, or pointed, depending on the tissue structure into which it will penetrate, the acceptable amount of ancillary damage, and/or other considerations.

The insertion implement 11 may have a handle 13 that, when squeezed, causes the inner tube 14 to extend distally away from the distal edge of the outer tube 16. FIG. 3 depicts the handle 13 as fully squeezed and, hence, the inner tube 14 is extended enough to expose the cavity 18, allowing the delivery device 10 to fall therefrom. When the inner tube 14 is so extended from the outer tube 16, the delivery device 10 suspends from a tether 12. When the inner tube 14 is retracted into the outer tube 16 prior to implantation, the delivery device 10 is retained within the cavity 18 by the outer tube 16. A seal, such as a lip rubbing seal, could be used between the inner and outer tubes to seal gas within the abdomen while the insertion implement 11 is in use.

In a preferred embodiment, the delivery device 10 is a tethered encapsulated containing biologically active agents. In that embodiment, the delivery device 10 includes a membrane 32 containing the biologically active agent, with a tether 12, or rod, extending therefrom. The tether 12 is of a length sufficient to reach from the membrane 32, at the treatment site 5, to a location external near the insertion site 2, and may be an extension of the cell vehicle.

The abdomen 20 may be insufflated during the process of implantation using, for example, a veress needle. A trocar, such as one created by Ethicon Endosurgery, in Cincinnati, Ohio, may be used to penetrate the abdomen 20 and/or serve as a vehicle for the insertion implement 11 and/or serve as a vehicle for the delivery device 10.

Figure 5:
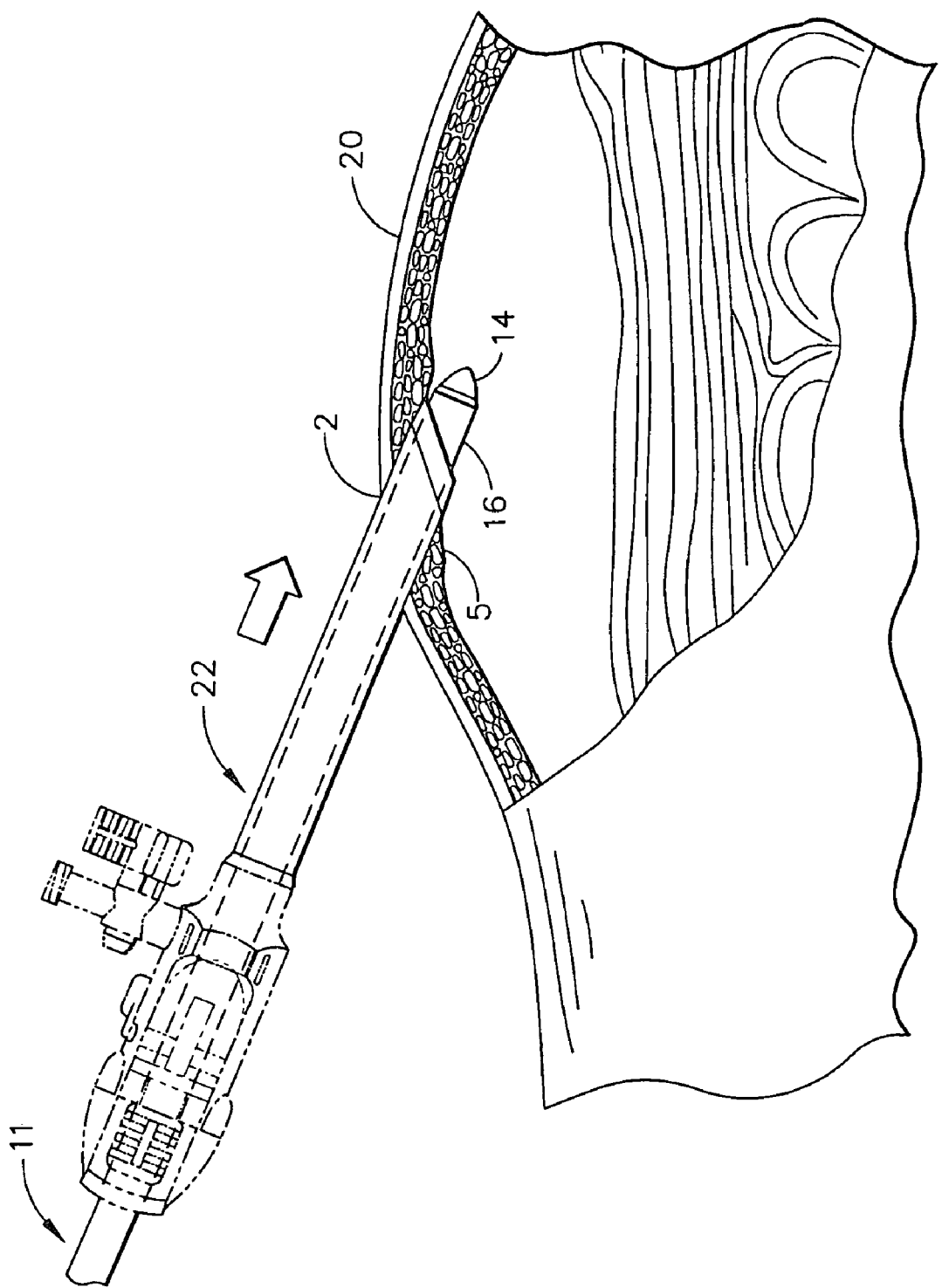
FIG. 5 shows the insertion implement in a cannula of FIG. 4 after entry into an abdomen according to an embodiment of the invention.

The distal end of the insertion implement 11 may be introduced into the abdomen 20 in a variety of ways. For example, a cannula 22, such as that of a trocar, may be positioned at the insertion site 2 with an obturator inserted therein to prevent material from entering the cannula 22 during insertion. After a cannula/obturator combination is inserted into the abdomen 20 at the insertion site 2, the obturator is removed, leaving the cannula 22 in the abdomen 20. Once the obturator has been removed, the cannula 22 is free to receive the insertion implement 11, which is generally of a predetermined shape to slidably fit within the central bore of the cannula 22. FIG. 5 depicts a trocar with an insertion implement 11 so inserted within its cannula 22 in the abdomen 20 of a subject. The use of a handle 13 advances the inner tube 14 distally within the outer tube 16.

Figure 4:
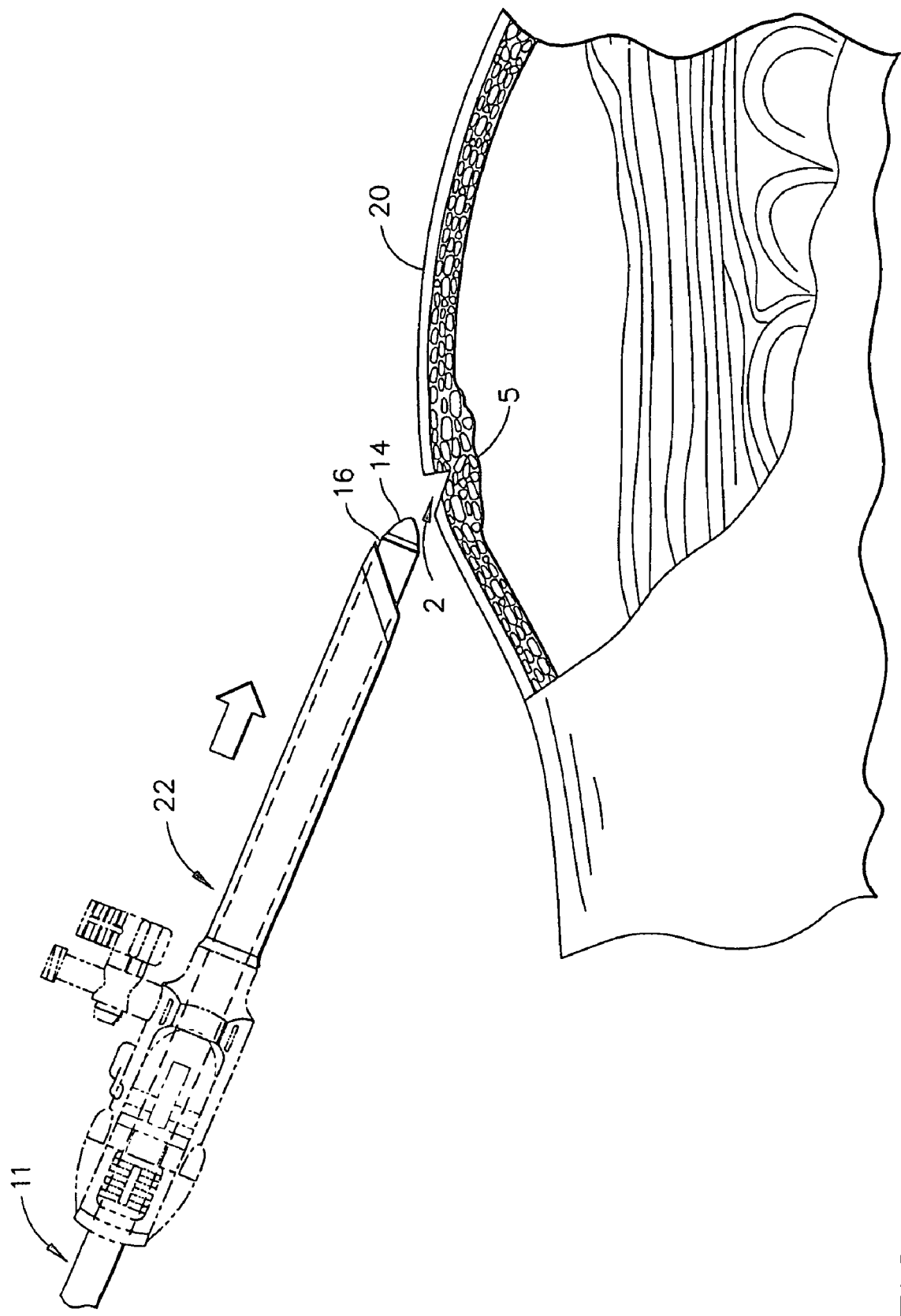
FIG. 4 shows an insertion implement in a cannula at entry into an abdomen according to an embodiment of the invention.

Alternatively, where the insertion implement 11 is capped at its distal end as shown in FIG. 3, the insertion implement 11 may act as the obturator to eliminate the steps of removing an obturator from the cannula 22 and subsequently inserting the insertion implement 11 in the cannula 22 after the cannula 22 has entered the abdomen 20. FIG. 4 shows the insertion implement 11 loaded in the cannula 22 of a trocar ready for use in the abdomen 20 of a subject, although the device may be used to implant objects in other parts of the body of a subject. When the insertion implement 11 is used as an obturator, the insertion implement will be loaded into the cannula 22 prior to penetration at the insertion site 2. This way, the insertion implement 11 may be introduced into the abdomen 20 upon the simultaneous insertion of the trocar with the insertion implement 11. FIG. 5 depicts a trocar with an insertion implement 11 inserted within cannula 22 in the abdomen 20 of a subject. The use of a handle 13 advances the inner tube 14 distally within the outer tube 16.

Alternatively, the insertion implement 11 may be inserted into an insertion site 2 without the use of a separate cannula 22.

Figure 6:
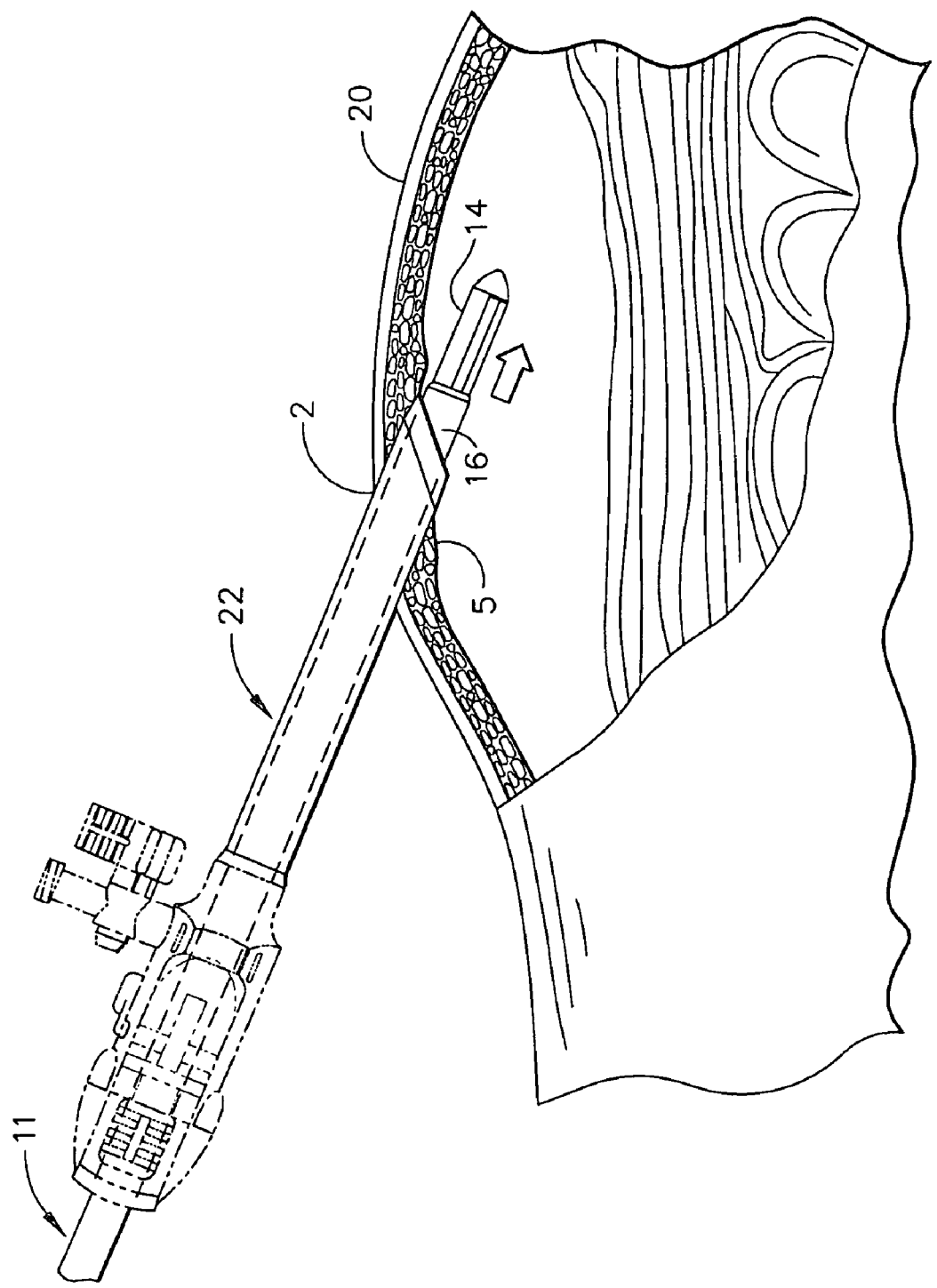
FIG. 6 shows extension of the inner tube of the insertion implement in a cannula of FIG. 4 according to an embodiment of the invention.

When the distal end of the insertion implement 11 has been introduced into the abdomen 20 through a cannula 22, such as that of a trocar, the distal end of the insertion implement 11 may be further extended from the cannula 22 as shown in FIG. 6. The inner tube 14 extends distally from the outer tube 16. A portion of the inner tube 14 and the delivery device 10 is still within outer tube 16, so that the outer tube 16 restrains the delivery device 10 within the cavity 18 of the inner tube 16. Prior to the extension of the inner tube 14, the abdomen 20 may be insufflated. This insufflation may aid in the deployment of the delivery device 10 from the cavity 18 of the inner tube 14.

Figure 7:
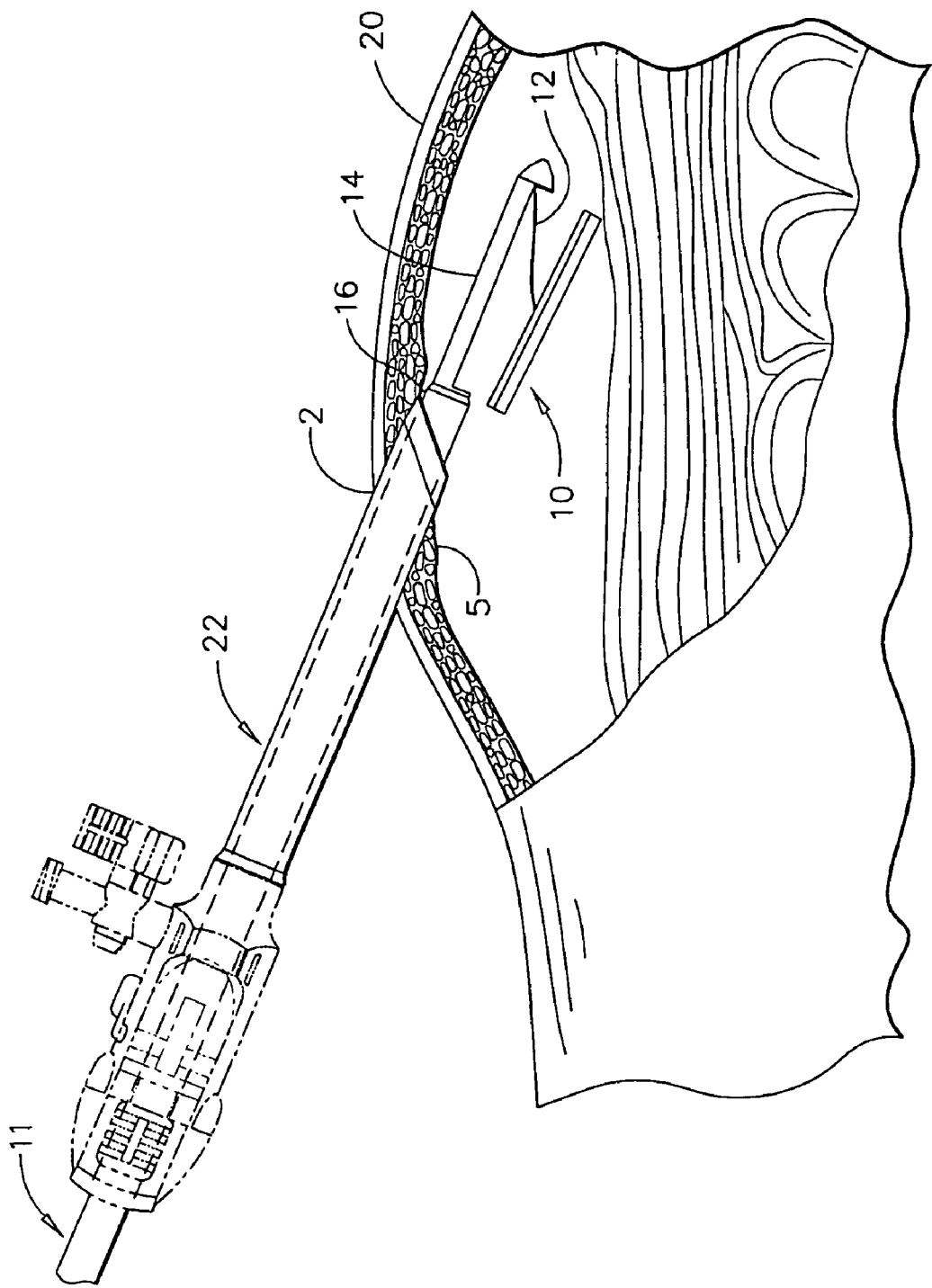
FIG. 7 shows a delivery device descending from the insertion implement in a cannula of FIG. 4 according to an embodiment of the invention.
Figure 8:
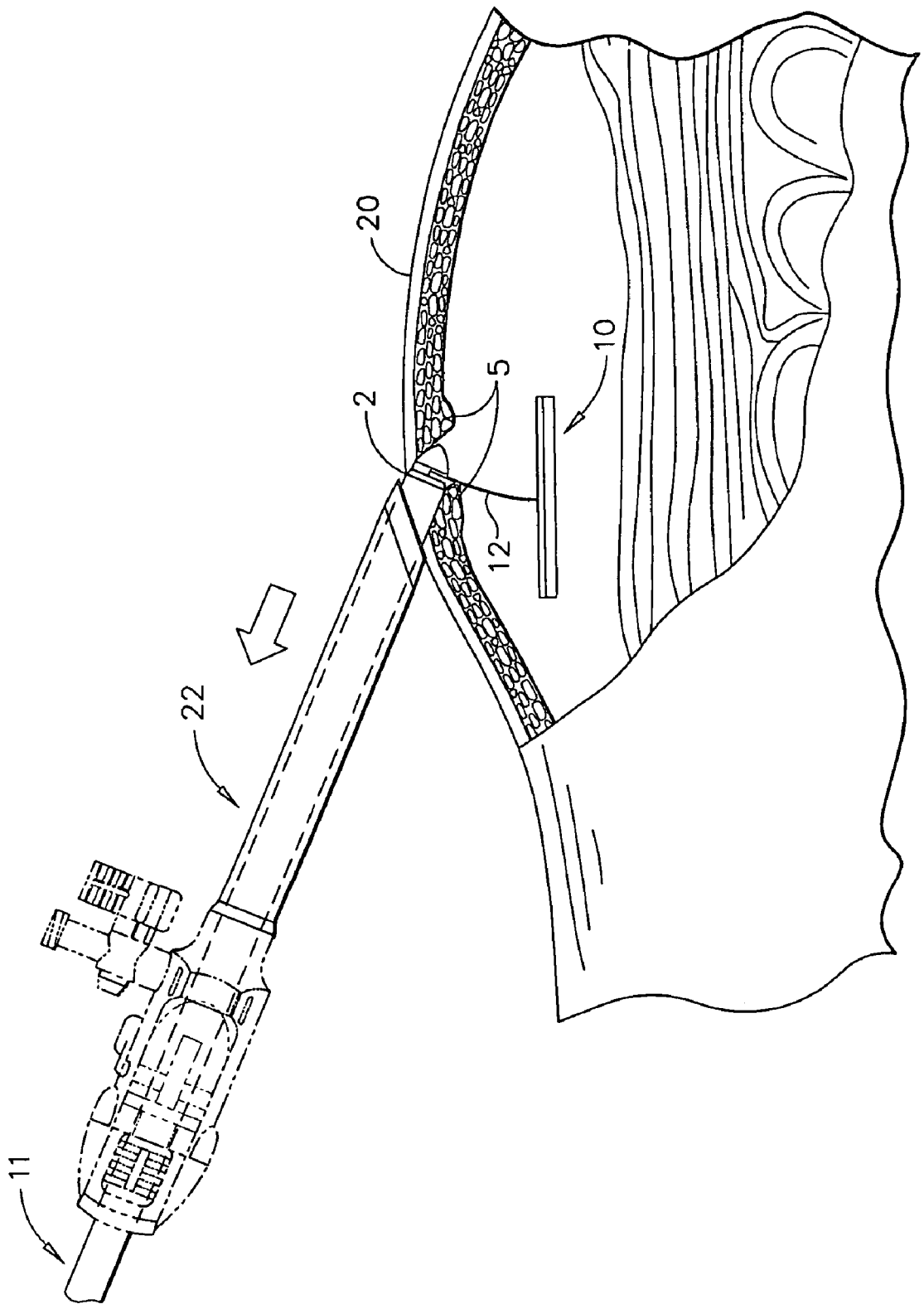
FIG. 8 shows the insertion implement in a cannula of FIG. 4 being removed from the abdomen according to an embodiment of the invention.

As shown in FIG. 7, the inner tube 14 may fully extend distally within the abdomen 20. The delivery device 10 may then fall from the inner tube 14, or alternatively, could be ejected from inner tube 14 by a spring or other means of deployment. A fluid or other material may be used to serve as a lubricant in the inner tube 14 to aid in the deployment of the delivery device 10. The delivery device 10 then suspends from a tether 12. After deployment of the delivery device 10, the inner tube 14 may be substantially retracted proximally back into the outer tube 16. Proximal retraction of the inner tube 14 may be temporarily ceased such that the tether 12 is not severed by pinching it off between the lip of the cavity 18 in the inner tube 14 and the distal lip of the outer tube 16. As shown in FIG. 8, the combination of the cannula 22 and the insertion implement 11 may then be pulled proximally through the wall of the abdomen 20.

Alternatively, after the delivery device 10 has been deployed, the combination of the cannula 22 and the insertion implement 11 may be pulled proximally through the wall of the abdomen 20 without retracting the inner tube 14 back into the outer tube 16. In other words, the inner tube 14 may be left fully or substantially extended at the time the combination of the cannula 22 and the insertion implement 11 is pulled proximally through the wall of the abdomen 20.

Figure 9:
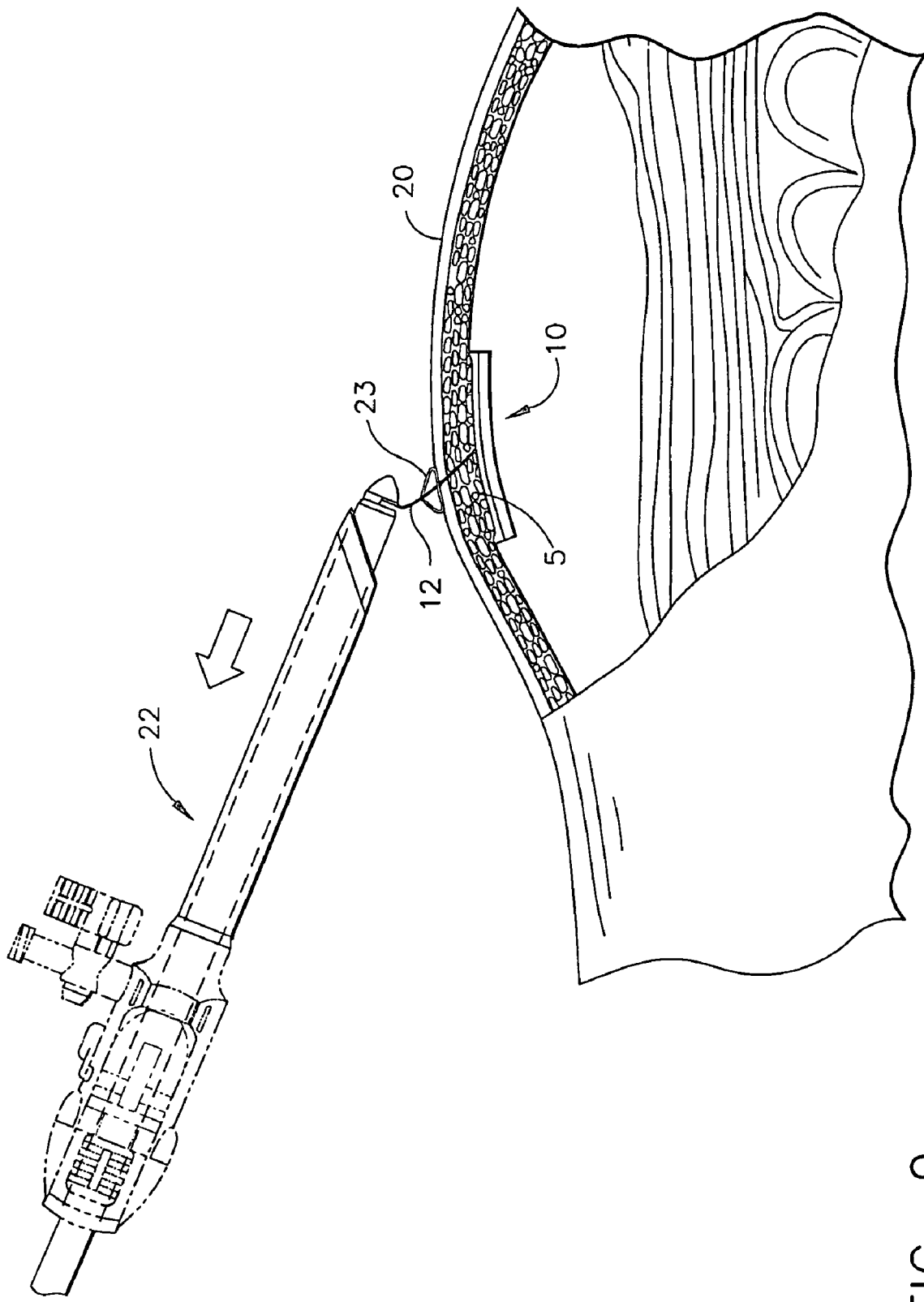
FIG. 9 shows a clip attached to a delivery device tether to hold it in place on the abdomen according to an embodiment of the invention.

FIG. 9 shows the delivery device 10 preloaded against the inner wall of the abdomen 20. It could be placed, for example, against the peritoneal wall by pulling the proximal end of the tether 12 proximally. Once the tether 12 is substantially taut, the tether 12 may be cinched in place with a clip 23. Alternatively, the tether 12 may be attached to the abdomen 20 or otherwise secured using a suture or other means known in the art. After the tether 12 is secured, it may be severed from the inner tube 14. As a final, optional step, a cap may be used to seal the insertion site 2 to prevent introduction of extraneous material through the insertion site 2. In a preferred form of the inventive method, the tether 12 allows the delivery device 10 to be retrieved from the treatment site 12.

The delivery device 10 may now have the advantages of the vascular tissue of the interior of the abdomen 20. Vascularization of the delivery device 10 may occur to feed the delivery device 10 with blood, or to cause exchange of any medication within the delivery device 10. Against the vascular tissue, the delivery device 10 may deliver drugs or therapeutic and/or prophylactic materials to the vascular tissue. The amount or rate of delivery of an agent across and/or into tissues is sometimes quantitated in terms of the amount of compound passing through a predetermined area of tissue, which is a defined area of intact unbroken living tissue. That area will usually be in the range of about 5 $cm^2$ to about 100 $cm^2$, more usually in the range of about 10 $cm^2$ to about 100 $cm^2$, still more usually in the range of about 20 $cm^2$ to about 60 $cm^2$. As will be appreciated by those of ordinary skill in the art, other ranges are possible.

Figure 10:
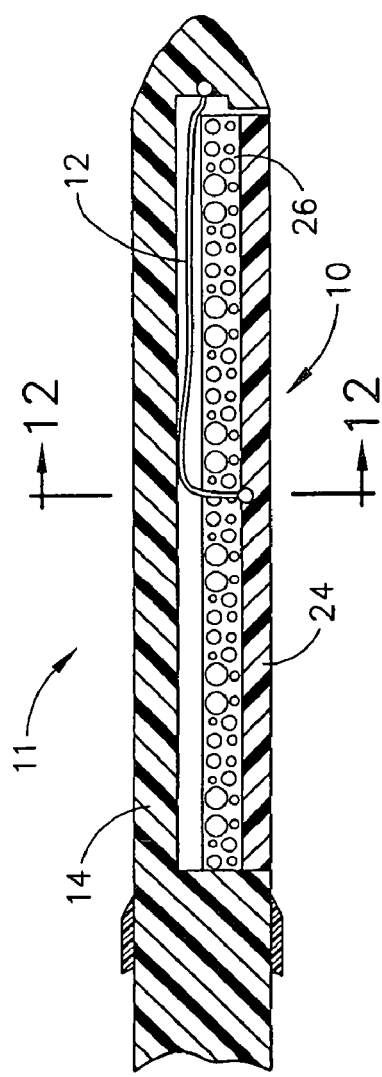
FIG. 10 shows a cross-sectional view of a delivery device and the distal end of an insertion implement according to an embodiment of the invention.

FIG. 10 shows a cross-section view of the distal end of the insertion implement 11. The delivery device 10 is within the inner tube 14. The delivery device 10 could be a biological construct, such as one disclosed in U.S. Pat. No. 4,902,295 by Walthall et al., or it could be a resilient, or sponge-like biomaterial 26 impregnated with useful pharmaceuticals or other materials. A softer material could be retained with a substrate 24 fashioned from, for example, a biocompatible and implantable plastic, such as polylactic acid or any other biocompatible and implantable material suitable for such use.

Figure 11:
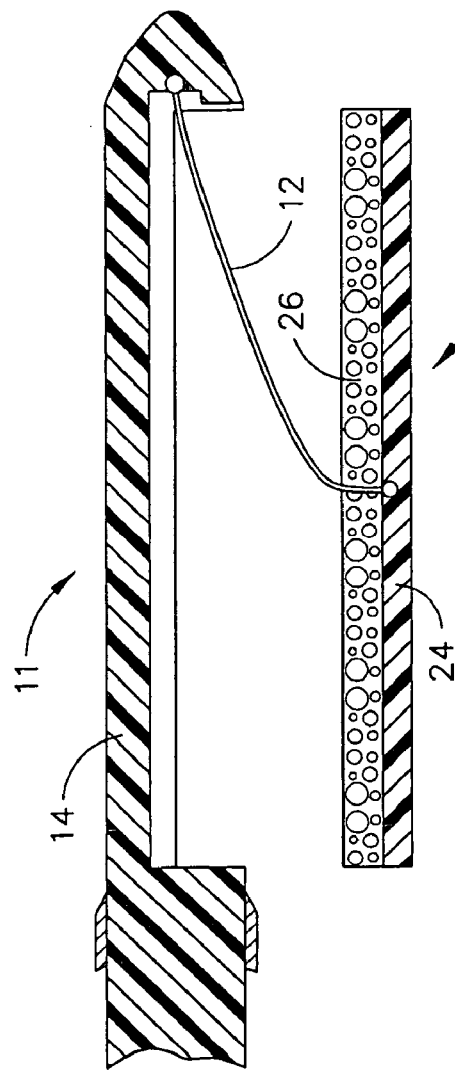
FIG. 11 is the delivery device and insertion implement of FIG. 8 with the delivery device detached from the inner tube of the insertion implement according to an embodiment of the invention.

FIG. 11 depicts the delivery device 10 detached from the inner tube 14 and suspended by a tether 12. The tether 12 may connect to both the delivery device 10 and the distal end of the inner tube 14 using, for example, a ball and socket joint to allow free maneuverability of the tether 12 while still attaching the parts. The tether 12 may also be attached to the delivery device 10 and the distal end of the inner tube 14 using any other methods available and known to those skilled in the art.

Figure 12:
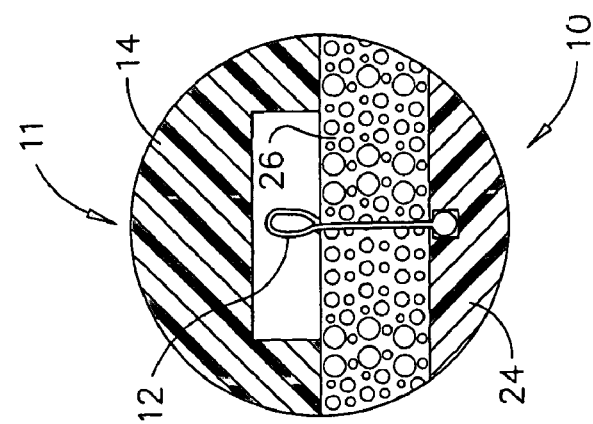
FIG. 12 depicts an embodiment of the delivery device with biological material extending to the outer diameter of the inner tube of the insertion implement.

FIG. 12 shows a cross-section taken transverse to a longitudinal axis of the inner tube 14. In one embodiment of the delivery device 10, biomaterial 26 could extend to the outer diameter of inner tube 14, to create a flat interface surface between the biomaterial 26 and the peritoneal wall of the abdomen 20.

FIG. 13 shows an alternate embodiment in which a substrate 24 follows the curvature of inner tube 14, so that the biomaterial 26 is enclosed. The substrate 24 follows an arcuate path of the outer diameter of the inner tube 14. This substrate 24 may further be comprised of or backed by a biocompatible resilient material that has shape memory, such that the delivery device 10 will substantially flatten out upon deployment into the body of a subject, while still being flexible enough to maximize surface contact with vascular tissue. Possible types of resilient materials having shape memory and methods of using them in a patch implantation context are disclosed by Seid in U.S. Pat. No. 5,254,133. Other materials having shape memory may be used.

FIG. 14 depicts the delivery device 10 of FIG. 13 deployed or prior to being loaded in the insertion implement 11. The material of the substrate 24 and of the biomaterial 26 is flexible enough to assume a substantially flat position upon deployment, so that after implantation the biomaterial 26 substantially abuts the peritoneal wall of the abdomen 20, maximizing the contact between the surface of the biomaterial 26 and the peritoneal wall of the abdomen 20.

In figures, the delivery device 10 generally has the shape of a rod. However, it should be appreciated that the delivery device 10 may have any shape which may accommodate the source of biologically active agent, or cells which release active agents, without causing undue trauma to the patient during implantation. The present delivery device 10 may be formed in a wide variety of shapes and combinations of suitable materials. A consideration in selecting a particular configuration for the delivery device when cells are present may be the access of oxygen and nutrients to the isolated cells or tissues, and passage of waste metabolites, toxins and the secreted product from the delivery device. The instant delivery device 10 may provide, in at least one dimension, sufficiently close proximity of any isolated cells in the core to the surrounding tissues of the recipient, including the recipient's bloodstream, in order to maintain the viability and function of the isolated cells. In general, the delivery device 10 may have a maximum depth-to-surface distance of no more than 5 mm in at least one dimension, with a maximum depth of 500 microns being preferred. Other depths may be employed without departing from the scope of the present invention. One or several delivery devices 10 may be required to produce a desired effect or effects in the recipient. Several alternative embodiments of implantable delivery devices 10 are shown. However, it will be appreciated that there are even more alternate embodiments of implantable delivery devices 10 that are possible and within the scope of the present invention, yet they are not shown in the figures.

In one embodiment, the implantable delivery device 10 of the present invention is of a sufficient size and durability for complete retrieval after implantation. To be contrasted with retrievable microcapsules, which have a typical maximum practical volume on the order of 1 microliter, the preferred delivery device 10 of the present invention is termed "macrocapsule". Such macrocapsules may have a core of a preferable minimum volume of about 1 to 10 μl and depending upon use are easily fabricated to have a value in excess of 100 μl. Other volumes are possible without departure from the present invention.

The delivery device 10, shown in further detail in FIGS. 13, 14, 15, and 16, includes biomaterial 26 filled with a secretory cell, preferably a cell that produces biologically active agents. In one embodiment, the delivery device 10 further includes a permeable, semi-permeable, or permselective membrane surrounding the biomaterial 26. The tether 12 may be generally constructed from an impermeable membrane material or may be coated with a material that makes the tether impermeable. In one embodiment, an impermeable protective barrier material may coat a portion of an outer membrane of the biomaterial 26. Exemplary protective barrier material includes polyethylene oxides, polypropylene oxides, silicon, hydrogels, and derivatives and mixtures thereof. It should be appreciated that the semipermeable membrane 32 may have alternative shapes that will accommodate the biomaterial 26. Alternatively, the delivery device may comprise a substantially solid formation of biomaterial without the need of any additional substrate and/or membranes, if such biomaterial is of sufficient rigidity and strength to maintain a form sufficient for maintaining contact with the subject's tissues.

The optional support structure 24, along with the biomaterial layer(s) 26 forms a three-dimensional structure that can promote tissue growth and neovascularization for drug delivery. It should be noted that the support structure 24, along with any optional membrane layers, may be composed of single or multiple layers of biocompatible materials, including, but not limited to, hydrogels, poly (2-hydroxyethyl methacrylate, pHEMA), hydroxyethyl methacrylate. (HEMA), polyacrylonitrile-polyvinyl chloride (PAN-PVC), polymers, polytetrafluoroethylene (PTFE), expanded polytetrafluoroethylene (ePTFE), polypropylene, high density polyethylene, polyurethane, polyester (Dacron), polyvinyl chloride, polyvinyl alcohol, acrylic copolymers, polysulfone, nylon, polyvinyl difluoride, polyanhydrides, silicone, polycarbonate, cellulose acetate, mixed ester cellulose, collagen, fibrin, poly (1-lysine), poly (L-lactic acid), hydroxyethylmetharcrylate, protein polymers, peptides polymers, hydroxyapeptite, alumina, zirconia, carbon fiber, aluminum, calcium phosphate, titanium, titanium alloy, nintinol, stainless steel, and CoCr alloy.

An outer membrane may be a polymer material and may include a surfactant, an anti-inflammatory agent, angiogenic factors, and/or an anti-oxidant. The specific type of polymer, surfactant, or other additive may depend on the material to be encapsulated and the configuration of the extrusion apparatus. Exemplary anti-inflammatory agents include, but are in no way limited to, corticoids such as cortisone and ACTH, dexamethasone, cortisol, interleukin-1 and its receptor antagonists, and antibodies to TGF-beta, to interleukin-1 (IL-1), and to interferon-gamma. Exemplary surfactants include, but are in no way limited to, Triton-X 100 from Sigma Chemicals, and Pluronics P65, P32, and P18. Exemplary anti-oxidants include, but are in no way limited to, vitamin C (ascorbic acid) and vitamin E. Exemplary angiogenic factors include, but are in no way limited to, fibroblast growth factor and nerve growth factor.

The optional membranes may be modified to further optimize drug delivery, such as by adding polyethylene oxide (PEO), heparin, albumin, tissue growth factors, angiogenic growth factors, and other interstitial tissue matrix substances, anti-inflammatory medications, and anti-rejection medications that promote and maintain healthy vascular tissue throughout the interconnecting pore structure, while minimizing the deposition of matrix proteins, fibrin, or collagen within the inner pore structure.

Angiogenic growth factors which may be used in the membranes include, but are not limited to, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, and Growth Hormone. Extracellular matrix proteins (ECM) placed within the outer membrane of the biomaterial structure provide cellular support, cellular polarity, cell orientation signals, and points of cellular adhesion to enhance vascular tissue ingrowth and angiogenesis.

In the event that the supply of active agents, e.g., cells secreting such factors, is spent, a delivery device 10 may be removed and replaced. Retrieval of an implanted delivery device 10 may be accomplished by pulling it out of the treatment site 5 by its tether 12. One way to effect removal is to use a pair of forceps after exposing the tether 12 by removal of a cap. Other retrieval devices and/or methods may be used. The cap may be located directly under the patient's epithelial tissues. The delivery device 10 may be replaced with a new insert in the event that additional therapy is required. Cells encapsulated within a delivery device 10 may also be retrieved if the cells cease to produce the biologically active agent, expire, or are no longer needed to correct and/or prevent a particular dysfunction.

A permeable portion (e.g., membrane) of a delivery device 10 is implanted at or near the target treatment site 5, while an impermeable portion may confine an active agent or agents to within the boundaries of the insert. A permeable portion may include a polymeric material having pores of a particular size (i.e., having a particular molecular weight cut-off) that excludes some molecules from passage therethrough, while permitting the passage of others. In this way, the diffusion of desired elements from the delivery device 10 to the treatment site is allowed, while the passage of deleterious elements such as viruses and various proteases is effectively barred. For example, delivery devices with pores having a molecular weight exclusion of from about 50 kD to about 300 kD may be useful, with those having pores with a molecular weight cut off of from about 25 kD to about 200 kD being particularly preferred. Other pore configurations and/or dimensions are possible without departure from the scope of the present invention.

The delivery device 10 may be composed of any biocompatible material having a desired pore size and being composed of materials which do not limit the activity of the substance embedded therein. Hydrophilic matrices such as, by way of example only, hydrogels (e.g., hydroxyethyl methacrylate, polyanhydrides, polyvinyl alcohol, and polyvinyl pyrrolidone) and hydrophobic matrices such as ethylene vinyl acetate may be particularly useful. In one embodiment, the implantable delivery device of the present invention is of a sufficient size and durability for complete retrieval after implantation.

The delivery device 10 may provide any biologically active agent that will satisfy the subject deficiency or remedy the dysfunction. Alternatively, the device may provide an active analog, active fragment, or active derivative of an active agent or agents, and/or may include a precursor which, after processing, provides the same activity as the factor in the appropriate in vivo location. The delivery device 10 may further include an agonist of the factor. Other agents may include insulin, Factor VIII, trophic factors such as, erythropoeitin and growth hormone, biological response modifiers, such as lymphokines and cytokines, enzymes, and antibodies from antibody-secreting cells. In addition, the capsule may contain multiple cell-types and cells, tissue, and/or other appropriate substance or substances.

An exemplary form of the delivery device 10 is a smooth, seamless delivery device 10 manufactured by coextrusion of a polymeric casting solution and a biomaterial solution. In this approach a multi-bore extrusion nozzle is used with the polymeric solution extruded from the outer bore and the active agent coextruded from an inner bore. In addition to containing active agent (or cells of tissue of the type described above), the active agent may include nutrients, such as fetal bovine, equine or porcine serum.

Any cells that secrete the biologically active agent that is therapeutic to a subject malady may be incorporated into the system of the invention. Additionally or alternatively, cells that secrete a biologically active agent that is prophylactic to a subject malady may be incorporated into the system of the invention. Various "growth factors" having the ability to stimulate cell growth, differentiation, and/or factor secretion may be co-implanted with the active agent-secreting cells to insure successful delivery of the desired agent or factor to the treatment site. These growth factors may be specific for a cell type or have a generalized effect on a number of different tissues. In the case of neurotransmitter-producing cells such as neurons, growth factors may act to maintain neurotransmitter production, as well as to promote cell maintenance and growth. Alternatively, growth factors may maintain nerve cells in a differentiated state. Useful cell growth factors include nerve growth factor (NGF), an array of fibroblast growth factors (FGF), platelet-derived growth factor (PDGF), brain-derived neuroprophic factor (BDNF), and epidermal growth factor (EGF), and ciliary growth factor, among many. In addition, effectors of various membrane receptors such as glutamate and nicotine may also be useful.

Further, any cells which have been genetically engineered to express a desired active agent, growth factor, and/or their agonists, precursors, derivatives, analogs, or fragments thereof, or other active agents having similar effector activities may also be useful in practicing this invention. Thus, in such an approach, the gene which encodes the active agent, or its analog or precursor may be either isolated from a cell line or constructed by DNA manipulation. The gene may then be incorporated into a plasmid which, in turn, may be transfected into a cell, such as a fibroblast, for expression. (See, e.g., Sambrook et al., Molecular Clonina (1989), herein incorporated by reference for further discussion of cloning delivery devices and gene manipulation procedures.) The cells that express the biologically active agent or factor may be grown in vitro until a suitable density is achieved.

FIG. 15 is a cross-sectional view of an alternate embodiment of the delivery device 10 in which the biomaterial 26 is near a substance 28 within a reservoir 29. In FIG. 15, a polymeric reservoir delivery device 10 containing active agent secreting cells is joined to the tether 12. The substance 28 could be, for example, a nutrient-rich material to allow cells within the delivery device 10 to survive until vascularization of delivery device 10 occurs. The nutrient-rich material could be, for example, fetal bovine, equine, or porcine serum, or any other material suitable for the purpose. Openings 30 are adjacent to the substance 28 to allow it to contact the biomaterial 26. Alternatively, the substance 28 can be a non-nutrient-rich material serving any suitable purpose.

FIG. 16 shows a cross-sectional view taken transverse to a longitudinal axis of the inner tube 14 of the embodiment of FIG. 15. In the embodiment of FIG. 16, the tether 12 may be a tube that may be used to replenish a reservoir 29. The reservoir 29 could also be replenished by other means, such as injection. The tether 12, after implantation, may be capped to keep a separation between the peritoneum and areas outside the body.

In one preferred embodiment, the delivery device 10 used is a thermoplastic PAN/PVC capsule with a liquid and cell core, having a wall thickness of greater than 25 microns, although a thickness of 25 microns or less may also be used. The core may also contain a hydrogel matrix or the like. The hydrogel matrix may be any commercially available three-dimensional network of hydrophilic polymers that are either covalently or ionically cross-linked. Any method of thermoplastic capsule preparation may be used, including hollow fiber preparation followed by filling with the cells and plugging and sealing using heat sealing. Alternatively, the capsules may be formed by coextrusion through a multi-lumen spinneret.

When the biologically active agent within the core of the biocompatible delivery device 10 comprises cells, the core is preferably constructed to provide a suitable local environment for the continued viability and function of the cells isolated therein. The instant delivery device 10 may be used to encapsulate a wide variety of cells or tissues, spanning the range from fully-differentiated, anchorage-dependent cells or primary tissues, through incompletely-differentiated fetal or neonatal tissues, to anchorage-independent transformed cells or cell lines. Unless otherwise specified, the term "cells" means cells in any form, including but not limited to cells retained in tissue, cell clusters, and individually isolated cells.

Implants of the delivery device 10 and contents thereof may retain functionality for greater than three months in vivo and in many cases for longer than a year. In addition, the delivery device 10 of the current invention may be prepared of sufficient size to deliver an entire therapeutic and/or prophylactic dose of a substance from a single or just a few (less than 10) implanted and easily retrievable delivery devices.

The core of the delivery device 10 may be constructed to provide a suitable local environment for the particular cells isolated therein. In some embodiments, the core comprises a liquid medium sufficient to maintain the cells. Liquid cores are particularly suitable for maintaining transformed cells. In other embodiments, the core comprises a gel matrix that immobilizes and distributes the cells, thereby reducing the formation of dense cellular agglomerations. The gel matrix may be composed of, by way of example only, hydrogel or extracellular matrix components.

Suitably, the core may be composed of a matrix formed by a hydrogel, which may stabilize the position of the cells in cell clumps. The term "hydrogel" herein refers to a three dimensional network of cross-linked hydrophilic polymers. The network may be in the form of a gel substantially composed of water, preferably but not limited to gels being greater than 90% water. Cross-linked hydrogels may also be considered solids because they do not flow or deform without appreciable applied shear stress.

Compositions which form hydrogels may fall into three classes for the purposes of this application. The first class carries a net negative charge and is typified by alginate. The second class carries a net positive charge and is typified by extracellular matrix components such as collagen and laminin. Examples of commercially available extracellular matrix components include Matrigel and Vitrogen. The third class is net neutral in charge. An example of a net neutral hydrogel is highly crosslinked polyethylene oxide, or polyvinylalcohol.

Cores made of a hydrogel matrix may be particularly suitable for maintaining cells or tissues which tend to form agglomerates or aggregates, such as the cells in islets of Langerhans, or adrenal chromaffin cells. The matrix may be of sufficient viscosity to maintain cell dispersion within the matrix. Optionally, the core of the instant delivery device may contain substances that support or promote the function of the isolated cells. These substances may include natural and/or synthetic nutrient sources, extracellular matrix (ECM) components, growth factors or growth regulatory substances, and/or a population of feeder or accessory cells or $O_2$ carriers such as hemoglobins and fluorocarbons.

Additionally, a population of feeder or accessory cells may be co-isolated within the delivery device. For example, hepatocytes may be coisolated with endothelial accessory cells.

Other embodiments and additions to the delivery device and methods are possible. Some are described below.

A delivery device 10 could include a marker to allow non-invasive localization of a delivery device 10 after implantation. Contrast material could be incorporated into a delivery device 10 to create the marker. The material could be, for example, gadolinium, a radio-opaque material, or microbubbles. The contrast materials could be different in different delivery devices 10 to identify the delivery devices 10 to track manufacturing numbers, or the type of delivery device 10. Delivery devices 10 could then be differentiated by the medication or cells they contain, time of manufacture, type of use, or other reasons for which differentiation is desirable.

Where the delivery device 10 is comprised of cells or a cell or tissue matrix, the constituent cells may be allogenic or xenogenic. In one embodiment, the cells are progenitor cells, e.g., stem cells and other pluripotent cells.

The insertion implement 11 could consist of only an inner tube 14 without an outer tube 16 if it used the cannula 22 of a trocar as an outer tube.

In general, methods for implanting or otherwise positioning active agent delivery devices 10 for delivery of an active agent are well known in the art. In general, placement of the active agent delivery device 10 may be accomplished using methods and tools that are well known in the art, and performed under aseptic conditions with at least some local or general anesthesia administered to the subject. Removal and/or replacement of active agent delivery devices 10 may also be accomplished using tools and methods that are readily available.

In one embodiment of the present invention, the delivery device 10 may be inserted in an abdomen 20 or other suitable site without the use of the insertion implement 11. By way of example only, an opening may be created at the insertion site 2 by any suitable method and/or device. The delivery device 10 may then simply be inserted by hand, or with the aid of any suitable device. FIG. 1 illustrates a delivery device 10 within an abdomen 20 without an insertion implement 11 or other device.

Figure 2:
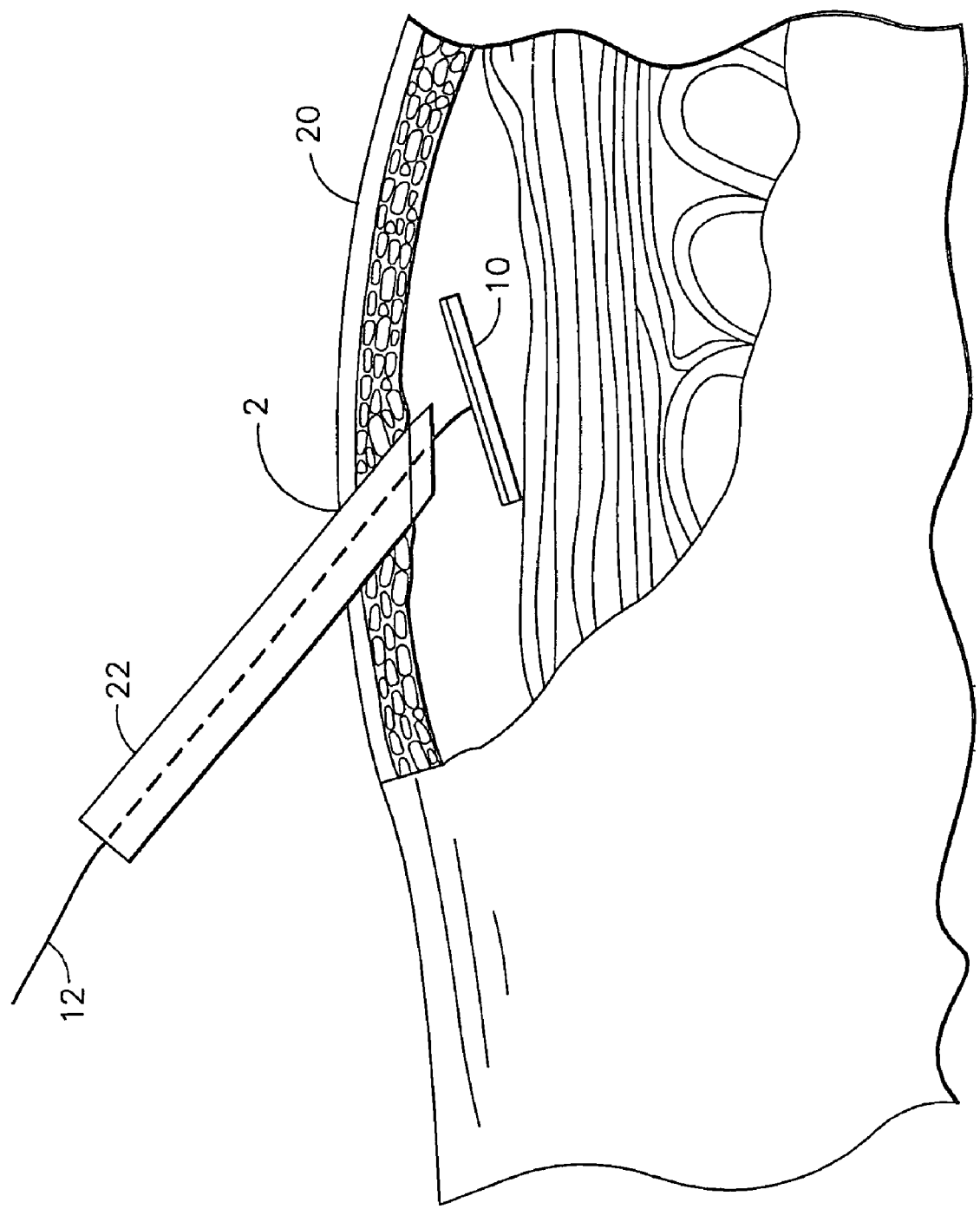
FIG. 2 is a view of a delivery device entered into an abdomen through a cannula according to an embodiment of the invention.

As shown in FIG. 2, the delivery device 10 may be inserted through a cannula 22 without the use of the insertion implement 11 shown in FIG. 3. In one form of the inventive method, prior to inserting the delivery device 10, the central bore of the cannula 22 is filled with a physiologically compatible solution, such as sterile saline. The delivery device 10 is then inserted within the cannula 22, and the solution acts as a lubricant to assure passage of the vehicle to the distal end of the cannula 22. In this embodiment, the insertion implement 11 shown in FIG. 3 is not used. Following insertion of the delivery device 10 within the cannula 22, a guide may be inserted to assist in positioning the delivery device 10 at the distal end of the cannula 22. The guide may be either the same obturator as that initially positioned within the cannula 22, a different obturator, a guide wire, or the like. The guide may be placed above the delivery device 10 within the cannula 22, and the delivery device 10 may be gently pushed into position at the distal end of the cannula 22. Finally, the cannula 22 is removed from the treatment site 5. If a guide or other device is used in the preceding step to position the delivery device 10, generally that device is removed in addition to the cannula 22. As with the obturator, the cannula 22 may be removed either by the cannula 22 mount or manually. The end result may be positioning of the delivery device 10 at the treatment site 5.

The system of the invention, useful for practicing the inventive method as described above, may include a cannula 22, at least one obturator, and a biological delivery device 10. Each of these is substantially as described above. The inclusion of a tether 12 to the biocompatible delivery device 10 should not affect delivery functioning or its biocompatibility. The entire length of the exemplary delivery device 10, including the tether 12, may be 2-10 cm. However, other lengths may be used without departure from the present invention.

The delivery device 10 may also be attached to vascular tissue other than peritoneum. For example, the delivery device 10 could be implanted on the omentum. In a device attached in this manner, the delivery device 10 could suspend from a tether 12 after the delivery device 10 enters the abdominal cavity. The delivery device 10 could then attach to the omentum, and a tether 12 could alternately be detached or remain attached to provide a port to the outside of the body.

The tether 12 may also include a collagen plug or similar means for preventing herniation of the tissue contiguous to the puncture tract created during the implantation. A preventative system for closing a percutaneous puncture with a collagen plug is disclosed by Kensey et al. in U.S. Pat. No. 5,531,759.

As used herein, a tether 12 may serve as a flexible link between an attachment tissue and the delivery device 10. Flexible tethers 12 for attaching the delivery device 10 to a substrate may satisfy two important requirements: (1) the need for providing immobilization of the delivery device 10 and tensioning of the delivery device 10 against vascularized tissues in order for the active agent effector molecules of the biomaterial 26 to exert an effect, and (2) biocompatibility of materials used for immobilization.

Examples of water-soluble, biocompatible polymers that may serve as tethers 12 include polymers such as synthetic polymers like polyethylene oxide (PEO), polyvinyl alcohol, polyhydroxyethyl methacrylate, polyacrylamide, and natural polymers such as hyaluronic acid, chondroitin sulfate, carboxymethylcellulose, and starch.

The length of a tether 12 may be limited only by the mechanical strength of the tether 12 used and the desired stability of a tethered biomaterial 26. It is expected that stronger tethers 12 may be made longer than weaker tethers, for example. It may also be desirable for tether 12 length and strength to be matched to give a desired half life to the tether 12, prior to breakage, and thereby adjust the half life of biomaterial action. The minimum tether 12 length also depends on the nature of the tether 12. A more flexible tether 12 may function well even if the tether 12 length is relatively short, while a stiffer tether 12 may need to be longer to allow effective connection between the biomaterial 26 and the tissues.

By way of example but not limitation, tethers 12 may have any length between 5 and 500 mm. Within this preferred range, it is contemplated that length ranges with different lower limits, such as 1, 2, 10, 15, 25, 30, 50, and 100 mm, may have useful characteristics. Other tether 12 lengths are possible without departure from the present invention.

In one embodiment, the delivery device 10 comprises a backing substrate 24 having the biomaterial 26 on one face. Backing substrates 24 may have any useful form including, but not limited to, fibers, woven fibers, shaped polymers, particles, sheet, sponge or membrane.

There may be two basic types of backing substrates 24 onto which active agents are preferably tethered. One class includes biocompatible materials that are not biodegradable, such as, by way of example only, polystyrenes, polyethylene vinyl acetates, polypropylenes, polymethacrylates, polyacrylates, polyethylenes, polyethylene oxides, glass, polysilicates, polycarbonates, polytetrafluoroethylene, fluorocarbons, nylon, silicon rubber, and stainless steel alloys. The other class of materials includes, but is not limited to, biocompatible, biodegradable materials such as polyanhydrides, polyglycolic acid, polyhydroxy acids such as polylactic acid, polyglycolic acid, and polylactic acid-glycolic acid copolymers, polyorthoesters, polyhydroxybutyrate, polyphosphazenes, polypropylfumerate, and biodegradable polyurethanes, proteins such as collagen and polyamino acids, and polysaccharides such as glycosaminoglycans, alginate, and carageenan, bone powder or hydroxyapatite, and combinations thereof.

The biodegradability of a substrate 24 may be used to regulate the length of time an active agent stimulates growth and to allow replacement of implanted substrate 24 with new tissue. For this purpose the substrate 24 with tethered active agents may be considered a scaffold upon which new tissue may form. As such, a degradable scaffold may be broken down as tissue replacement proceeds. Once released from the substrate 26, an active agent may be internalized or may diffuse away from the target cells. Such planned degradation may be especially useful in the context of implanted compositions, used to stimulate tissue replacement, by limiting the amount of tissue growth and eliminating the need to remove the tissue scaffold. For implantation in the body, preferred degradation times are typically less than one year, more typically in the range of weeks to months. Other degradation times are possible without departure from the present invention.

In some embodiments, attachment of cells to the substrate 24 may be enhanced by coating the substrate 24 with compounds such as extracellular membrane components, basement membrane components, agar, agarose, gelatin, gum arabic, collagen types I, II, III, IV, and V, fibronectin, laminin, glycosaminoglycans, mixtures thereof, and other materials known to those skilled in the art of cell culture.

The tether 12 and/or the substrate 24 may be made from a bioabsorbable material such as, by way of example only, the materials disclosed by Tormala et al. in U.S. Pat. No. 6,406, 498. In one embodiment, the passive sustained release active agent drug delivery system comprises a matrix comprising a polymer and an active agent. Preferably, the active agent is present in a concentration of at least about 5 weight percent based on the weight of the matrix. Other concentrations are possible without departure from the present invention. In another embodiment, the matrix further comprises a permeation promoter.

In another embodiment, the active agent delivery system comprises a patch suitable for adhering to tissue, the patch having a matrix-containing reservoir. In another embodiment, patch comprises (a) an impermeable backing layer; (b) an active agent layer element having a hollow space; and (c) a top surface having a microporous or semi-permeable membrane. Furthermore, this may comprise an adhesive layer on the top surface for adhering to the tissues. The reservoir may be formed by a hollow space between the covering layer and the membrane. Generally, the membrane comprises an inert polymer. The reservoir may comprise an open-pore foam, a closed-pore foam, a fabric layer, or a web layer. Optionally, the matrix is self-adhesive. The microporous or semi-permeable membrane may consist of an inert polymer, for example polypropylene, polyvinyl acetate or silicone.

In another embodiment, the passive active agent drug delivery system comprises: (a) an impermeable backing layer; and (b) an active-agent-containing matrix layer; wherein the active substance in the active-agent-containing layer comprises a prodrug form or active form of at least one active agent; optionally a permeation promoter; and a matrix polymer.

Also provided is a method for the passive sustained release administration of an active or prodrug form of active agent to a subject in need of treatment, the method comprising contacting the tissue of the patient with a sustained release device as described herein.

Delivery of Active Agents

The present invention provides compositions and methods that effect the transfer of compounds, including drugs and other biologically active agents, into and across tissues, e.g., one or more layers of an animal epithelial or endothelial tissue. The methods involve contacting the tissue with a active agent delivery device 10 that includes the compound of interest. The methods and compositions are useful for delivery of drugs and other biologically active molecules, and also for delivery of imaging and diagnostic molecules. The methods and compositions of the invention may be particularly useful for delivery of compounds that require trans-epithelial or trans-endothelial transport to exhibit their biological effects, and that by themselves, are unable, or only poorly able, to exhibit biological activity.

The delivery devices 10 and methods of the invention provide significant advantages over previously available methods for obtaining tissue delivery of compounds of interest. Compositions and methods of the present invention may have particular utility in the area of human and veterinary therapeutics. Generally, administered dosages may be effective to deliver picomolar to micromolar concentrations of the therapeutic composition to the effector site. Appropriate dosages and concentrations may depend on factors such as the therapeutic composition or drug, the site of intended delivery, and the route of administration, all of which may be derived empirically according to methods well known in the art. Further guidance may be obtained from studies using experimental animal models for evaluating dosage, as are known in the art.

Administration of the compounds of the invention with a suitable pharmaceutical excipient as necessary may be carried out via any of the accepted modes of administration. Suitable sites of administration thus include, but are not limited to, peritoneal and omentum. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

Active agents can be provided in any of a variety of formulations within the biomaterial compatible with transmucosal/transepithelial delivery, provided that such formulation is stable (i.e., not subject to degradation to an unacceptable amount at body temperature). The concentration of active agents in the formulation may vary from about 0.1 wt. % to about 80 or even 100 wt %. The active agents can be provided in any form suitable to be carried by the controlled drug delivery device and released for distribution, e.g., solid, semi-solid, gel, liquid, suspension, emulsion, osmotic dosage formulation, diffusion dosage formulation, erodible formulation, etc.

The compositions may include a conventional pharmaceutical carrier or excipient and may additionally include other medicinal agents, carriers, adjuvants, and the like. Preferably, the composition will be about 5% to 95% by weight of a compound or compounds of the invention, with the remainder consisting of suitable pharmaceutical excipients. Other compositions are possible without departure from the present invention. Appropriate excipients may be tailored to the particular composition and route of administration by methods well known in the art.

In some embodiments, the composition may contain, among other things, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

Methods for preparing such dosage forms are known or will be apparent to those skilled in the art; for example, see Remington's Pharmaceutical Sciences, supra., and similar publications. The composition to be administered may, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which may vary depending on the individual and condition being treated. By way of example only, a therapeutically effective daily dose may be from 0.1 to 100 mg/kg of body weight per day of drug. Many conditions may respond to administration of a total dosage of between about 1 and about 30 mg/kg of body weight per day, or between about 70 mg and 2100 mg per day for a 70 kg person. Other dosages may be administered without departure from the present invention.

The delivery devices 10 of the invention make possible the delivery of biologically active and diagnostic agents into vascularized tissue within a subject's body. This ability to deliver active agents in a sustained, long-term delivery method may greatly enhance the efficacy of compounds such as antibacterials, antifungals, antivirals, antiproliferatives, immunosuppressives, vitamins, analgesics, hormones, and the like.

In general, administration of active compounds according to the invention can be sustained release for several hours (e.g., 2 hours, 12 hours, or 24 hours to 48 hours or more), to several days (e.g., 2 to 5 days or more), to several months or years. Typically, delivery can be continued for a period ranging from about 1 month to about 12 months or more. The active compounds may be administered to an individual for a period of, for example, from about 2 hours to about 72 hours, from about 4 hours to about 36 hours, from about 12 hours to about 24 hours, from about 2 days to about 30 days, from about 5 days to about 20 days, from about 7 days or more, from about 10 days or more, from about 100 days or more, from about 1 week to about 4 weeks, from about 1 month to about 24 months, from about 2 months to about 12 months, from about 3 months to about 9 months, from about 1 month or more, from about 2 months or more, or from about 6 months or more; or other ranges of time, including incremental ranges, within these ranges, as needed.

Cytotoxic and immunosuppressive drugs may constitute an additional class of drugs for which the delivery devices 10 of the invention may be useful. These agents are commonly used to treat hyperproliferative diseases such as psoriasis, as well as for immune diseases such as bullous dermatoses and leukocytoclastic vasculitis. Examples of such compounds include, but are not limited to, antimetabolites such as methotrexate, azathioprine, fluorouracil, hydroxyurea, 6-thioquanine, mycophenolate, chlorambucil, vinicristine, vinblasrine and dactinomycin. Other examples iinclude alkylating agents such as cyclophosphamide, mechloroethamine hydrochloride, carmustine, taxol, tacrolimus and vinblastine are additional examples of useful biological agents, as are dapsone and sulfasalazine. Ascomycins, such as Cyclosporine, FK506 (tacrolimus), and rapamycin (e.g., U.S. Pat. No. 5,912,253) and analogs of such compounds are of particular interest (e.g., Mollinson et al., Current Pharm. Design 4(5):367-380 (1998); U.S. Pat. Nos. 5,612,350; 5,599,927; 5,604,294; 5,990,131; 5,561,140; 5,859,031; 5,925,649; 5,994,299; 6,004,973 and 5,508,397). Cyclosporins include cyclosporin A, B, C, D, G and M. See, e.g., U.S. Pat. Nos. 6,007,840; and 6,004,973. Another aspect of the invention comprises delivery of taxane- and taxoid anticancer compositions, which are particularly useful for inhibiting growth of cancer cells.

The delivery devices 10 may be useful for treating conditions such as lupus erythematosus (both discoid and systemic), cutaneous dermatomyositis, porphyria cutanea tarda and polymorphous light eruption. Agents useful for treating such conditions include, for example, quinine, chloroquine, hydroxychloroquine, and quinacrine.

The delivery devices 10 of the invention may also useful for transdermal delivery of antiinfective agents. For example, antibacterial, antifungal and antiviral agents may be used with the delivery devices 10. Antibacterial agents may be useful for treating conditions such as acne, cutaneous infections, and the like. Antifungal agents may be used to treat tinea corporis, tinea pedis, onychomycosis, candidiasis, tinea versicolor, and the like. Examples of antifungal agents include, but are not limited to, azole antifungals such as itraconazole, myconazole and fluconazole. Examples of antiviral agents include, but are not limited to, acyclovir, famciclovir, and valacyclovir. Such agents may be useful for treating viral diseases, e.g., herpes.

Another example of a biologically active agent for which the delivery devices 10 of the invention may be desirable are the antihistamines. These agents are useful for treating conditions such as pruritus due to urticaria, atopic dermatitis, contact dermatitis, psoriasis, and many others. Examples of such reagents include, for example, terfenadine, astemizole, lorotadine, cetirizine, acrivastine, temelastine, cimetidine, ranitidine, famotidine, nizatidine, and the like. Tricyclic antidepressants may also be delivered using the delivery devices 10 of the invention.

Pain relief agents and local anesthetics constitute another class of compounds for which the delivery devices 10 of the invention may enhance treatment. Lidocaine, bupibacaine, novocaine, procaine, tetracaine, benzocaine, cocaine, and the opiates, are among the compounds that may be uses with the delivery devices 10 of the invention.

In one embodiment, the active agent formulation comprises a cardiac drug including, but is not limited to: angiogenic factors, growth factors, calcium channel blockers, antihypertensive agents, inotropic agents, antiatherogenic agents, anti-coagulants, beta-blockers, anti-arrhythmic agents, anti-inflammatory agents, sympathomimetic agents, phosphodiesterase inhibitors, diuretics, vasodilators, thrombolytic agents, cardiac glycosides, antibiotics, antiviral agents, antifungal agents, agents that inhibit protozoans, antineoplastic agents, and steroids.

The term "anti-arrhythmia agent" or "anti-arrhythmic" refers to any drug used to treat a disorder of rate, rhythm or conduction of electrical impulses within the heart. The term "angiogenic agent" (or "angiogenic factor") means any compound that promotes growth of new blood vessels. Angiogenic factors include, but are not limited to, a fibroblast growth factor, e.g., basic fibroblast growth factor (bFGF), and acidic fibroblast growth factor, e.g., FGF-1, FGF-2, FGF-3, FGF-4, recombinant human FGF (U.S. Pat. No. 5,604,293); a vascular endothelial cell growth factor (VEGF), including, but not limited to, VEGF-1, VEGF-2, VEGF-D (U.S. Pat. No. 6,235,713); transforming growth factor-alpha; transforming growth factor-beta; platelet derived growth factor; an endothelial mitogenic growth factor; platelet activating factor; tumor necrosis factor-alpha; angiogenin; a prostaglandin, including, but not limited to PGE 1, PGE2; placental growth factor; GCSF (granulocyte colony stimulating factor); HGF (hepatocyte growth factor); IL-8; vascular permeability factor; epidermal growth factor; substance P; bradykinin; angiogenin; angiotensin II; proliferin; insulin like growth factor-1; nicotinamide; a stimulator of nitric oxide synthase; estrogen, including, but not limited to, estradiol (E2), estriol (E3), and 17-beta estradiol; and the like. Angiogenic factors further include functional analogs and derivatives of any of the aforementioned angiogenic factors. Derivatives include polypeptide angiogenic factors having an amino acid sequence that differs from the native or wild-type amino acid sequence, including conservative amino acid differences (e.g., serine/threonine, asparagine/glutamine, alanine/valine, leucine/isoleucine, phenylalanine/tryptophan, lysine/arginine, aspartic acid/glutamic acid substitutions); truncations; insertions; deletions; and the like, that do not substantially adversely affect, and that may increase, the angiogenic property of the angiogenic factor. Angiogenic factors include factors modified by polyethylene glycol modifications; acylation; acetylation; glycosylation; and the like. An angiogenic factor may also be a polynucleotide that encodes the polypeptide angiogenic factor. Such a polynucleotide may be a naked polynucleotide or may be incorporated into a vector, such as a viral vector system such as an adenovirus, adeno-associated virus or lentivirus systems.

Antibiotics are among the biologically active agents that may be useful when used with the delivery devices 10 of the invention, particularly those that act on invasive bacteria, such as *Shigella, Salmonella*, and *Yersinia*. Such compounds include, for example, norfloxacin, ciprofloxacin, trimethoprim, sulfamethyloxazole, and the like.

Anti-neoplastic agents may also be delivered by the delivery devices 10 of the invention. These include, for example, cisplatin, methotrexate, taxol, fluorouracil, mercaptopurine, donorubicin, bleomycin, and the like.

The delivery devices 10 may also be useful for delivering biologically active and diagnostic agents across the blood brain barrier. The agents may be useful for treating ischemia (e.g., using an anti-apoptotic drug), as well as for delivering neurotransmitters and other agents for treating various conditions such as schizophrenia, Parkinson's disease, pain (e.g., morphine, the opiates). The 5-hydroxytryptamine-receptor antagonist is useful for treating conditions such as migraine headaches and anxiety.

The delivery devices 10 may also be useful for delivering biologically active agents by sustained or controlled delivery and/or release and capable of inducing or promoting a feeling of satiety in a subject. Generally, in order to induce satiety, the active agent is selected from the group consisting of nutrients and pharmacological agents. The nutrients are generally selected from the group consisting of foodstuffs, amino acids, peptides, proteins, lipids, carbohydrates, vitamins and minerals.

Suitable protein sources include, but are not limited to, milk, soy, rice, meat (e.g., animal), vegetable (e.g., beet, pea, potato), egg (egg albumen), gelatin, and fish. Suitable intact proteins include, but are not limited to, soy based, milk based, casein protein, whey protein, rice protein, beef collagen, pea protein, potato protein and mixtures thereof. Suitable protein hydrolysates also include, but are not limited to, soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, a combination of animal and vegetable protein hydrolysates, and mixtures thereof. Hydrolyzed proteins (protein hydrolysates) are proteins that have been hydrolyzed or broken down into shorter peptide fragments and amino acids.

Favored proteins include extensively hydrolyzed protein hydrolysates prepared from acid or enzyme treated animal and vegetable proteins, such as, casein hydrolysate, whey hydrolysate, casein/whey hydrolysate, soy hydrolysate, and mixtures thereof. By "extensively hydrolyzed" protein hydrolysates it is meant that the intact protein is hydrolyzed into peptide fragments whereby a majority of peptides fragments have a molecular weight of less than 1000 Daltons. More preferably, from at least about 75% (preferably at least about 95%) of the peptide fragments have a molecular weight of less than about 1000 Daltons.

The amino acids may be one or more of aspartic acid, alanine, arginine, asparagine, cysteine, glycine, glutamic acid, glutamine, histidine, isoleucine, leucine, lysine, methionine, phenylalanine, proline, serine, threonine, tryptophan, tyrosine, and valine. Preferred amino acids are L-phenylalanine, L-tryptophan, L-tyrosine, L-cystine, L-taurine, L-methionine, L-arginine, and L-carnitine. More preferred amino acids are L-phenylalanine and L-tryptophan.

Suitable foodstuffs, amino acids, peptides, proteins, lipids, carbohydrates, vitamins and minerals may vary widely and are well known to those skilled in the art of making pediatric formulas. Carbohydrates useful in the present invention include mono-, di- and polysaccharides. Preferred saccharides include, e.g., glucose, fructose, mannose, galactose, sucrose, maltose, lactose, maltodextrins and glucose polymers. Preferably, the carbohydrate is maltose. Suitable carbohydrates may thus include, but are not limited to, hydrolyzed, intact, naturally and/or chemically modified starches sourced from corn, tapioca, rice or potato in waxy or non waxy forms; and sugars.

Suitable vitamins include, but are not limited to, vitamins A, E, C, D, K, the B complex vitamins, pantothenic acid, thiamin, niacin, niacinamide, riboflavin, iron and biotin. Minerals include, but are not limited to, calcium, chromium, phosphorus, sodium, chloride, magnesium, manganese, iron, copper, zinc, selenium, and iodine. Salts may also be used. Suitable salts include, but are not limited to, sodium, potassium, magnesium and calcium.

Suitable lipids include, but are not limited to, coconut oil, soy oil, corn oil, olive oil, safflower oil, high oleic safflower oil, MCT oil (medium chain triglycerides), sunflower oil, high oleic sunflower oil, palm oil, palm olein, canola oil, lipid sources of arachidonic acid and docosahexaneoic acid, and mixtures thereof. Lipid sources of arachidonic acid and docosahexaneoic acid include, but are not limited to, marine oil, egg yolk oil, and fungal oil.

Depending on the desired results, the active agent may include an active lipid; a serotonin, serotonin agonist, or serotonin re-uptake inhibitor; peptide YY or a peptide YY functional analog; calcitonin gene-related peptide (CGRP) or a CGRP functional analog; an adrenergic agonist; an opioid agonist; a combination of any of any of these; or an antagonist of a serotonin receptor, peptide YY receptor, CGRP receptor; adrenoceptor and/or opioid receptor; and/or glucagon-like peptide 1 (GLP1).

Preferably, in order to induce a feeling of satiety in the subject, the active agent is one or more agents selected from the group of an active lipid; a serotonin, serotonin agonist, or serotonin re-uptake inhibitor; peptide YY or a peptide YY functional analog; GLP 1 peptides and GLP 1 analogs, calcitonin gene-related peptide or a functional analog; CGRP or a CGRP functional analog; an adrenergic agonist; an opioid agonist; or a combination of any of these, which is delivered in an amount and under conditions such that the cholinergic intestino-fugal pathway, at least one prevertebral ganglionic pathway, the adrenergic efferent neural pathway, the serotonergic interneuron and/or the opioid interneuron are activated thereby. Serotonin, or 5-hydroxytryptamine (5-HT) is preferably used at a dose of 0.005-0.75 mg/kg of body mass. Serotonin re-uptake inhibitors include Prozac or Zoloft.

Serotonin receptor antagonists include antagonists of 5-HT3, 5-HT1P, 5-HT1A, 5-HT2, and/or 5-HT4 receptors. Examples include ondansetron or granisetron, 5HT3 receptor antagonists (preferred dose range of 0.04-5 mg/kg), deramciclane, or alosetron. 5-HT4 receptor antagonists are preferably used at a dose of 0.05-500 picomoles/kg.

Peptide YY (PYY) and its functional analogs are preferably delivered at a dose of 0.5-500 picomoles/kg. PYY functional analogs include PYY (22-36), BIM-43004 (Liu, C D, et al., J. Surg. Res. 59(1):80-84 [1995]), BIM-43073D, BIM-43004C (Litvak, D. A. et al., Dig. Dis. Sci. 44(3):643-48 [1999]). Other examples are also known in the art (e.g., U.S. Pat. No. 5,604,203). PYY receptor antagonists preferably include antagonists of Y4/PP1, Y5 or Y5JPP2/Y2, and most preferably Y1 or Y2. (e.g., U.S. Pat. No. 5,912,227) Other examples include BIBP3226, CGP71683A (King, P. J. et al., J. Neurochem. 73(2):641-46 [1999]).

Adrenergic agonists include norepinephrine. Adrenergic or adrenoceptor antagonists include β-adrenoceptor antagonists, including propranolol and atenolol. They are preferably used at a dose of 0.05-2 mg/kg.

Opioid agonists include delta-acting opioid agonists (preferred dose range is 0.05-50 mg/kg, most preferred is 0.05-25 mg/kg); κ-acting opioid agonists (preferred dose range is 0.005-100 microgram/kg); μ-acting opioid agonists (preferred dose range is 0.05-25 μg/kg); and episilon-acting agonists.

Opioid receptor antagonists include μ-acting opioid antagonists (preferably used at a dose range of 0.05-5 microgram/kg); κ-opioid receptor antagonists (preferably used at a dose of 0.05-30 mg/kg); Δ opioid receptor antagonists (preferably used at a dose of 0.05-200 microgram/kg); and ε-opioid receptor antagonists. Examples of useful opioid receptor antagonists include naloxone, naltrexone, methylnaltrexone, nalmefene, H2186, H3116, or fedotozine, i.e., (+)-1-1 [3,4,5-trimethoxy)benzyloxymethyl]-1-phenyl-N,N-dimethylpropylamine. Other useful opioid receptor antagonists are known (e.g., U.S. Pat. No. 4,987,136).

In one embodiment, the active agent is one or more active lipid. As used herein, "active lipid" encompasses a digested or substantially digested molecule having a structure and function substantially similar to a hydrolyzed end-product of fat digestion. Examples of hydrolyzed end products are molecules such as diglyceride, monoglyceride, glycerol, and most preferably free fatty acids or salts thereof.

In a preferred embodiment, the active agent is an active lipid comprising a saturated or unsaturated fatty acid. Fatty acids contemplated by the invention include fatty acids having between 4 and 24 carbon atoms.

Examples of fatty acids contemplated for use in the practice of the present invention include caprolic acid, caprulic acid, capric acid, lauric acid, myristic acid, oleic acid, palmitic acid, stearic acid, palmitoleic acid, linoleic acid, linolenic acid, trans-hexadecanoic acid; elaidic acid, columbinic acid, arachidic acid, behenic acid eicosenoic acid, erucic acid, bressidic acid, cetoleic acid, nervonic acid, Mead acid, arachidonic acid, timnodonic acid, clupanodonic acid, docosahexaenoic acid, and the like. In a preferred embodiment, the active lipid comprises one or more of oleic acid, dodecanoic acid and glycerol monooleate.

Also preferred are active lipids in the form of pharmaceutically acceptable salts of hydrolyzed fats, including salts of fatty acids. Sodium or potassium salts are preferred, but salts formed with other pharmaceutically acceptable cations are also useful. Useful examples include sodium- or potassium salts of caprolate, caprulate, caprate, laurate, myristate, oleate, palmitate, stearate, palmitolate, linolate, linolenate, trans-hexadecanoate, elaidate, columbinate, arachidate, behenate, eicosenoate, erucate, bressidate, cetoleate, nervonate, arachidonate, timnodonate, clupanodonate, docosahexaenoate, and the like. In a preferred embodiment, the active lipid comprises an oleate and/or dodecanate salt. Sodium dodecanoate or sodium dodecylsulfate are also preferred active ingredients.

The delivery devices of the invention are also useful for delivery of diagnostic imaging and contrast agents into and across one or more layers of an epithelial and/or endothelial tissue. Examples of diagnostic agents include substances that are labeled with radioactivity, such as 99 mTc glucoheptonate, or substances used in magnetic resonance imaging (MRI) procedures such as gadolinium doped chelation agents (e.g. Gd-DTPA). Other examples of diagnostic agents include marker genes that encode proteins that are readily detectable when expressed in a cell (including, but not limited to, (beta-galactosidase, green fluorescent protein, luciferase, and the like. A wide variety of labels may be employed, such as radionuclides, fluors, enzymes, enzyme substrates, enzyme cofactors, enzyme inhibitors, ligands (particularly haptens), etc.

Small organic molecule therapeutic agents may be advantageously delivered as described herein, across an epithelial or endothelial tissue. For example, delivery of highly charged agents, such as levodopa (L-3,4-dihydroxy-phenylalanine; L-DOPA) may benefit by linkage to delivery devices as described herein. Peptoid and peptidomimetic agents are also contemplated (e.g., Langston (1997) DDT2:255; Giannis et al. (1997) Advances Drug Res. 29:1). Also, the invention is advantageous for delivering small organic molecules that have poor solubilities in aqueous liquids, such as serum and aqueous saline. Thus, compounds whose therapeutic efficacies are limited by their low solubilities may be administered in greater dosages according to the present invention, and may be more efficacious due to higher uptake levels by cells.

The devices and methods of the invention are particularly suited for transport into and across one or more layers of an epithelial or endothelial tissue for a number of macromolecules, including, but not limited to proteins, nucleic acids, polysaccharides, and analogs thereof. Exemplary nucleic acids include oligonucleotides and polynucleotides formed of DNA and RNA, and analogs thereof, which have selected sequences designed for hybridization to complementary targets (e.g., antisense sequences for single- or double-stranded targets), or for expressing nucleic acid transcripts or proteins encoded by the sequences. Such molecules may be used in a variety of therapeutic regimens, including enzyme replacement therapy, gene therapy, and anti-sense therapy, for example.

Another class of macromolecules that may be transported across one or more layers of an epithelial or endothelial tissue is exemplified by proteins, and in particular, enzymes. Therapeutic proteins include, but are not limited to replacement enzymes. Therapeutic enzymes include, but are not limited to, alglucerase, for use in treating lysozomal glucocerebrosidase deficiency (Gaucher's disease), alpha-L-iduronidase, for use in treating mucopolysaccharidosis I, alpha-N-acetyl-glucosamidase, for use in treating sanfilippo B syndrome, lipase, for use in treating pancreatic insufficiency, adenosine deaminase, for use in treating severe combined immunodeficiency syndrome, and triose phosphate isomerase, for use in treating neuromuscular dysfunction associated with triose phosphate isomerase deficiency. In another embodiment, the invention is useful for delivering immunospecific antibodies or antibody fragments to the cytosol to interfere with deleterious biological processes such as microbial infection.

Peptides to be delivered by the methods described herein include, but should not be limited to, effector polypeptides, receptor fragments, and the like. Examples include peptides having phosphorylation sites used by proteins mediating intra-cellular signals. Examples of such proteins include, but are not limited to, protein kinase C, RAF-1, p21Ras, NF-kappaB, C-JUN, and cytoplasmic tails of membrane receptors such as IL-4 receptor, CD28, CTLA-4, V7, and MHC Class I and Class II antigens.

In addition to the above ingredients, the therapeutic composition of the invention may generally contain various pharmaceutically acceptable additives as well as a pharmaceutically acceptable carrier or base necessary for dispersion of such substances. Said additives include but are not limited to pH control agents, such as arginine, sodium hydroxide, glycine, hydrochloric acid, citric acid, etc., local anesthetics represented by benzyl alcohol, isotonizing agents such as sodium chloride, mannitol, sorbitol, etc., adsorption inhibitors such as Tween 80 etc., solubilizers such as cyclodextrins and derivatives thereof, stabilizers such as serum albumin etc., and reducing agents such as glutathione and so on.

Since a variety of proteolytic enzymes are present in the administration environment, there are cases in which a protease inhibitor may be advantageously incorporated in the composition of the invention to preclude degradation of the physiologically active peptide or protein and thereby insure a more enhanced bioavailability. The protease inhibitor mentioned above includes but is not limited to gabaxate mesylate, α1-antitrypsin, aprotinin, leupepsin, α2-macroglobulin, pepstatin and egg white or soybean trypsin inhibitor. These inhibitors may be used alone or in combination. The protease inhibitor may be incorporated in the hydrophilic polymer, coated on the surface of the dosage form that is to contact the tissue or incorporated in a superficial phase of the surface.

The therapeutic composition of the present invention may be further supplemented with an absorption promoter that assists in the absorption and diffusion of the physiologically active peptide or protein. The absorption promoter may be any promoter that is pharmaceutically acceptable. Thus, there may be mentioned sodium salicylate and salicylic acid derivatives (acetyl salicylate, choline salicylate, salicylamide, etc.), amino acids and salts thereof (e.g. monoaminocarboxlic acids such as glycine, alanine, phenylalanine, proline, hydroxyproline, etc., hydroxyamino acids such as serine etc., acidic amino acids such as aspartic acid, glutamic acid, etc. and basic amino acids such as lysine etc., inclusive of their alkali metal or alkaline earth metal salts), N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts), substances which are generally used as emulsifiers (e.g. sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters and so on. While the mechanism of absorption promotion may vary with different absorption promoters, the proper one for a long-term administration may be selected according to each combination of the physiologically active peptide or protein and other ingredients. The above-mentioned additives may be dispersed in the pharmaceutically acceptable base or vehicle.

The base for the therapeutic composition of the present invention may be a hydrophilic compound having a capacity to disperse the peptide and said additives. The molecular weight of such hydrophilic compound is preferably, but not limited to, not less than 1000, more preferably not less than 10000, and even more preferably not less than 100000. The compound may be a pharmaceutically acceptable substance and may typically include but is not limited to the following compounds. Thus, copolymers of polycarboxylic acids or salts thereof or carboxylic anhydrides (e.g. maleic anhydride) with other monomers (e.g. methyl (meth)acrylate, acrylic acid, etc.), hydrophilic vinyl polymers such as polyvinyl acetate, polyvinyl alcohol, polyvinylpyrrolidone, etc., cellulose derivatives such as hydroxymethylcellulose, hydroxypropylcellulose, etc., and natural polymers such as chitosan, collagen, sodium alginate, gelatin, hyaluronic acid, etc. and nontoxic metal salts thereof. Further, synthetic fatty acid esters such as polyglycerin fatty acid esters, sucrose fatty acid esters, etc. may also be mentioned.

These hydrophilic polymers may be used alone or in combination and partial crystallization, ionic bonding, crosslinking or the like may impart a necessary structural integrity. Any of these hydrophilic polymers may be molded into a film form and applied to the tissue.

As the base for use in the present invention, a biodegradable synthetic polymer may be employed as a dispersion base containing the active agent. The biodegradable polymer may typically include but is not limited to polylactic acid, poly (lactic acid-glycolic acid) copolymer, polyhydroxybutyric acid, poly(hydroxybutyric acid-glycolic acid) copolymer and mixtures thereof. These biodegradable polymers may be molded into a film or tablet for application to the vascular tissue.

For peptides, the physiologically acceptable peptide is dispersed in such a dosage form base in the per se known manner. The release of the active peptide from such a dosage form may be by diffusion, disintegration of said biodegradable polymer or the associated formulation of water channels. A further possible mechanism is that when the glass transition temperature of such a biodegradable polymer is near or lower than the body temperature, the biodegradable polymer applied to the living body becomes softened to cause the release of the physiologically active peptide at an accelerated rate of diffusion. A further promotion of absorption may be insured by an ingenious combination of biodegradable polymer and cytidine nucleotide derivative.

The pharmaceutical composition of the present invention may contain a hydrophilic low molecular weight compound. Such a hydrophilic low molecular weight compound may provide continuous passages through which the water-soluble physiologically active peptide or protein may diffuse through the base to the body surface where it is absorbed. The passageways may be either microscopic or macroscopic, that is to say the whole dosage form may serve as a passageway.

The hydrophilic low molecular weight compound may be any such compound that absorbs moisture from the tissues or the administration atmosphere and dissolves the water-soluble active peptide. The molecular weight of said hydrophilic low molecular weight compound is typically, but not limited to, not more than 10000 and preferably not more than 3000. Thus, as polyol compounds, there may be mentioned oligo-, di- and monosaccharides such as sucrose, mannitol, lactose, L-arabinose, D-erythrose, D-ribose, D-xylose, D-mannose, D-galactose, lactulose, cellobiose, gentibiose, etc. may be mentioned. As other polyol compounds, there may be mentioned glycerin and polyethylene glycol (average molecular weight 200-3000). Other examples of said hydrophilic low molecular weight compound include N-methylpyrrolidone, alcohols (e.g. oligovinyl alcohol, ethanol, ethylene glycol, propylene glycol, etc.). These hydrophilic low molecular weight compounds are used alone or in combination.

The above-mentioned hydrophilic polymer, biodegradable polymer, hydrophilic low molecular weight compound, absorption promoter, protease inhibitor and additives are preferably selected according to the amino acid composition of the active peptide, the steric structure thereof and/or other factors.

The amount of physiological peptide or protein in the compositions of this invention is typically a quantity that provides an effective amount of the peptide or protein to produce the physiological activity for which the peptide or protein is being administered.

The amount of the physiologically active peptide or protein to be contained in the therapeutic composition of the present invention may be selected according to the activity of the particular substance and its therapeutically effective dose but in consideration of the fact that the bioavailability of any active substance may never be 100%, that is to say the administered dose of the active peptide is not completely absorbed, it may be preferable to incorporate a slightly larger amount than the desired dosage.

Active Agent Producing Cells

In an alternate implantable active agent delivery system comprises (a) a delivery device 10 comprising a carrier and eucaryotic cells that produce at least one therapeutic agent. Optionally, the delivery device 10 may include a stimulating element operatively coupled to the delivery device 10 for stimulating the release of the therapeutic agent from the delivery device 10. In another embodiment, the delivery device 10 further comprises a sensing element for monitoring at least one physiological property of a patient in which the system is implanted and communicating with the stimulating element to stimulate the release of the therapeutic agent from the delivery device 10. The carrier may be selected from a group comprising stents, vascular grafts, stent grafts, synthetic patches, infusion sleeves, and catheters.

The eucaryotic cells may reside within a polymer composition. The implantable system may also include a polymer composition capable of dehydration and rehydration. In one embodiment, the polymer compositions may be selected from a group consisting of fibrins, collagens, alginates, polylactic acids, polyglycolic acids, celluloses, hyaluronic acids, polyurethanes, silicones, polycarbonates, mixtures and copolymers thereof. In one embodiment, the eucaryotic cells are selected from a group consisting of endothelial cells, fibroblasts, and mixtures thereof. Generally, the cells may be autologous, but do not have to be autologous. Preferably, the cells are genetically engineered. Generally, the delivery device further comprises a containment vehicle in which the cells are located.

Cells suitable for use in the present invention include a wide variety of eucaryotic cells that produce therapeutic agents, or may be genetically engineered to produce therapeutic agents. Ideally, such cells are also able to secrete these agents, particularly upon the application of a stimulus, such as an electrical and/or other stimulus.

Suitable cells for use in the present invention typically include mesenchymal or mesodermal cells, including, but not limited to endothelial cells and fibroblasts, whether they are autologous or allogeneic, genetically engineered or nonengineered. Mixtures of such cells may also be used.

Suitable cells also include progenitor cells, e.g., stem cells and other pluripotent cells.

Endothelial cells and fibroblasts are preferred because they have been shown to be suitable for use in ex vivo gene transfer. Ex vivo gene transfer (also referred to herein as ex vivo gene therapy) is a process by which cells are removed from the body using well known techniques, genetically manipulated, usually through transduction or transfection of nucleic acid into the cells in vitro, and then returned to the body for therapeutic purposes. This contrasts with in vivo gene therapy, where a gene transfer vector is administered to the patient resulting in genetic transfer into cells and tissues in the intact patient. Ex vivo techniques are well known to one of skill in the art.

Ex vivo gene therapy is an effective approach because the target cells to be used in the procedure may be manipulated as needed to optimize gene transfer efficiency and thus the effectiveness of the overall procedure. However, the ex vivo approach may only be utilized for those cell types that may be readily retrieved from the body, cultured ex vivo, and then returned to the body. Such cells include blood and marrow cells, liver hepatocytes, skin fibroblasts, muscle myoblasts, and vascular endothelial cells. Thus, endothelial cells and fibroblasts, which may be efficiently infected by retroviral vectors in vitro, and then transplanted back into the host to achieve gene transfer in vivo, are particularly preferred for use in the present invention.

Autologous endothelial cells may be particularly desirable. Vascular endothelial cells have been removed from a patient and transduced ex vivo with a retroviral vector designed for expression of β-galactosidase as a reporter gene, as disclosed in Nabel et al., Science, 244, 1342-1344 (1989). Such genetically engineered cells may be reintroduced into a patient.

In one embodiment of the present invention, endothelial cells are obtained from a patient and grown in cell culture. During proliferation in cell culture, they are infected with a genetically engineered retrovirus, which integrates the gene for the drug to be locally delivered into the chromosomes of the endothelial cells. This may be accomplished, for example, according to the teachings of U.S. Pat. No. 5,674,722. For the treatment of coronary artery disease (CAD), candidate genes include the gene encoding wild-type tissue plasminogen activator and the gene encoding protein C, for example.

There are a wide variety of methods that may be used to deliver nucleic acid to the eucaryotic cells if they are to be modified to secrete a desired agent. These are well known to one of skill in the art. The desired nucleic acid may be inserted into an appropriate delivery vehicle, such as, for example, an expression plasmid, cosmid, YAC vector, and the like. There are a number of viruses, live or inactive, including recombinant viruses that may also be used. A retrovirus may be genetically modified to deliver any of a variety of genes. Adenovirus has been used in a variety of experiments to deliver nucleic acid capable of directing and expressing protein in a cell.

Exemplary nucleic acids that may function as nucleic acid for incorporation into the cells include, but are not limited to, nucleic acid operably encoding a protein, polypeptide, or peptide to deliver a therapeutic effect to a cell. The nucleic acid may include an entire gene or a portion of a gene. Exemplary genes include, but are not limited to, the active form of the nitric oxide synthase (a protein that is known to relax blood vessels and prevent clot formation), and prostaglandin H synthase (to restore an endogenous inhibitor of platelet aggregation and vasoconstriction following injury to endothelium) and insulin-producing genes.

There are a variety of disorders that may be treated using the systems and devices of this invention. Examples of these disorders include, but are not limited to, diabetes and insulin-related diseases (targeting pancreatic islet cells), damage associated with myocardial infarction or aneurysms (targeting fibroblast growth factor or transforming growth factor, and protease, respectively), atherosclerosis (targeting high density lipoprotein), and hypercoagulable states (targeting tissue-plasminogen activator).

The gene sequence of the nucleic acid delivered by the virus, including nucleic acid encoding proteins, polypeptide or peptide may be available from a variety of sources including GenBank (Los Alamos National Laboratories, Los Alamos, N.Mex.), EMBL databases (Heidelberg, Germany), and the University of Wisconsin Biotechnology Center, (Madison, Wis.), published journals, patents and patent publications. All of these sources may be resources readily accessible to those of ordinary skill in the art. The gene sequence may be obtained from cells containing the nucleic acid fragment (generally, DNA) when a gene sequence is known. The nucleic acid may be obtained either by restriction endonuclease digestion and isolation of a gene fragment, or by polymerase chain reaction (PCR) using oligonucleotides as primers either to amplify cDNA copies of mRNA from cells expressing the gene of interest or to amplify cDNA copies of a gene from gene expression libraries that are commercially available. Oligonucleotides or shorter DNA fragments may be prepared by known nucleic acid synthesis techniques and from commercial suppliers of custom oligonucleotides such as Amitof Biotech Inc. (Boston, Mass.), or the like. Those skilled in the art will recognize that there are a variety of commercial kits available to obtain cDNA from mRNA (sources including, but not limited to Stratagene, La Jolla, Calif. and Invitrogen, San Diego, Calif.). Similarly, there are a variety of commercial gene expression libraries available to those skilled in the art including libraries available form Stratagene, and the like. General methods for cloning, polymerase chain reaction and vector assembly are available from Sambrook et al. eds. (Molecular Cloning: A Laboratory Manual, 1989 Cold Spring Harbor Laboratory Press, Cold Spring Harbor, N.Y.) and Innis, et al. eds. (PCR Strategies, 1995, Academic Press, New York, N.Y.).

In a further embodiment, the present invention provides an implantable bioartificial active secretion system for providing a physiological secretion necessary for functionality of a physiologic activity of a living-being host. The system first includes a housing having an inlet with an external opening thereto and an outlet with an external opening therefrom. This housing may be implantable at least partially within the host such that the inlet and outlet openings are positionable in fluidic communication with tissue fluid of the host and the tissue fluid may be received into the housing and thereafter dispensed from the housing. A chamber may be disposed within the housing between the inlet and outlet and in communication therewith, and may contain a plurality of physiologically active, autonomously functioning, live secretory cells for producing the physiological secretion.

In a further embodiment, disposed within the housing is a periodically-operating pump apparatus for drawing initial tissue fluid through the inlet from the host for contact with the physiologically active cells within the chamber for pick up and regulation of the physiological secretion, and for dispensing resulting tissue fluid bearing the physiological secretion through the outlet and into the host. Finally, inlet and outlet filter systems in operational communication with the external openings of the inlet and outlet may have openings therethrough sized for prohibiting passage of immune system cells, immunoglobulins, and complement system components of the host.

The tissue fluid drawn to be in contact with the live secretory cells may generally reflect host requirements for the particular physiological secretion. Thus, in treating diabetes for example, peritoneal fluid may be drawn since it is known that peritoneal fluid reflects blood glucose levels, whereby peritoneal fluid contacts secretory cells that are pancreatic beta cells, which produce insulin for peritoneal-fluid uptake and return for routing to regulate such glucose levels. The secretory cells preferably are encapsulated with a permeable medium through which cellular nutrient as well as cellular metabolic waste may pass and likewise through which the physiological secretion may pass, but not through which immune system cells may pass on the off-chance that such cells passed through the inlet filter. Encapsulation increases the loading density of the cells and their surface interaction with the fluid. Depending upon the specific application, secretory-cell life span many times may be up to about two years, after which time replacement cells are introduced.

A pump apparatus, preferably includes a plurality of sequentially disposed, peristaltic-like activated and deactivated, elasticized pump tubes for peristaltic-like moving therewithin the initial tissue fluid and the tissue fluid bearing the physiological secretion through the device, may be included. Peristaltic-like pumping may be accomplished electromagnetically by a programmed controller disposed with the housing and thus implanted, and/or by a programmed controller situated outside the patient and in proximity to the implanted housing. In either configuration, power may be intermittently applied to replicate peristaltic movement of tissue fluid through the pump tubes and thus in moving contact with the live secretory cells situated within the housing. The tissue fluid may reflect whether a need is present for the particular secretion provided by the secretory cells (e.g., glucose level for insulin-secreting cells), whereby the secretory cells will naturally respond to the conveyed need and automatically produce a quantity of secretion specific to this need as sensed by the secretory cells. The tissue fluid picks up this secretion as it contacts the secretory cells, and thereafter is delivered within the host. Finally, when the tissue fluid indicates less need for the secretion (e.g., the required activity of the secretion has been completed for the time being), the secretory cells sense such reduced need as the tissue fluid continues in contact therewith, and the secretory activity naturally ceases.

As is apparent, the implantable bioartificial active secretion system here defined may significantly replicate natural metabolic function by employing live secretory cells as both sensor and provider of physiologic balance. Such live-cell employment may eliminate external guesswork with respect to quantity and timing of secretion-product injection or other type introduction since actual cells make a natural determination of need followed by a natural production and natural release of an exactly necessary quantity of the secretory product.

In an exemplified embodiment, the present invention may provide for the physiologically beneficial delivery-on-demand of insulin for glucose metabolism within a patient suffering from Type I diabetes. Particularly, the system may function in the capacity of an artificial pancreas and may be implanted at a site within the peritoneal cavity such that peritoneal fluid may enter the device. The device may be located within the peritoneal cavity. This placement permits relatively easy, rapid, and complete retrieval in the event of any delivery device failure or malfunction.

Implantation may be generally carried out under local anesthesia. It is to be noted that peritoneal fluid is chosen for insulin-need determination because a change of glucose concentration in peritoneal fluid is in the same direction, same amount, and relatively same time factor as in blood. The insulin secretory cells may be present as beta cells or as tissue as described above.

In the preferred embodiment, groups of cells, with total count of at least about 1,000,000 cells, are contained within the delivery device 10. Generally, movement of the peritoneal fluid may continue through the delivery device 10 for contact with the insulin secretory cells. These secretory cells naturally react to the glucose level of the peritoneal fluid and naturally secrete insulin into the peritoneal fluid as determined by the secretory cells to be needed for proper glucose metabolism. Additionally, oxygen and nutrients may be passed to the secretory cells while metabolic waste from the secretory cells passes into the peritoneal fluid. Secretory-cell life spans are, of course, dependent upon a number of factors including proper nutrition and oxygen delivery, waste product removal, and extent of secretion called for by the host being. When cell effectiveness diminishes or ceases, however, the devices may be relatively easily retrieved and replaced by fresh units, with the device then returned to its implanted site.

As is apparent from the above description, the secretion system here defined may bioartificially emulate a naturally occurring secretion system by providing live secretion-producing cells for sensing and producing secretions at levels naturally determined because of such live authenticity. In addition to such implantation of secretion-producing cells, other media, including drugs, medicines, and/or enzymes, for treating or preventing diseases in accord with physiological demands, may likewise be administered by employing the system here described and within which the chosen media is placed. Thus, while these illustrative and presently preferred embodiments of the invention have been described in detail herein, it is to be understood that the inventive concepts may be otherwise variously embodied and employed and that the appended claims are intended to be construed to include such variations except insofar as limited by the prior art.

In summary, numerous benefits have been described which result from employing the concepts of the invention. The foregoing description of one or more embodiments of the invention has been presented for purposes of illustration and description. It is not intended to be exhaustive or to limit the invention to the precise form disclosed. Obvious modifications or variations are possible in light of the above teachings. The one or more embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

The invention claimed is:

1. An implantable active agent delivery device for providing an active agent to a subject, the delivery device comprising:
   (a) a reservoir, wherein the reservoir contains a substance, wherein the reservoir includes openings, wherein the openings are adjacent to the substance;
   (b) a biomaterial, wherein the biomaterial is near the substance within the reservoir, wherein the openings of the reservoir allow the substance in the reservoir to contact the biomaterial, the biomaterial comprising:
      (i) a core,
      (ii) a front surface, and
      (iii) a back surface,
      wherein the front surface of the biomaterial is adapted to be held substantially adjacent to vascular tissue within the subject,
      wherein the biomaterial is capable of administering an active agent or of providing a metabolic or immunologic function to the subject;
   (c) an external selectively permeable jacket surrounding the core, the jacket comprising a biocompatible membrane having a molecular weight cutoff permitting passage of molecules of an active agent to and from the core through the jacket to adjacent vascular tissue within the subject; and
   (d) a tether coupled with the biomaterial, wherein the tether is configured to anchor the biomaterial at an implantation site, wherein the tether comprises a tube configured to replenish the reservoir.

2. The device of claim 1, wherein the tether is adapted to hold the biomaterial substantially adjacent to vascular tissue.

3. The device of claim 1, wherein the tether material is bioabsorbable.

4. The device of claim 1 wherein the device further comprises a radio-opaque marker material.

5. The device of claim 2 wherein the device is adapted for delivery of active agent to the peritoneum.

6. The device of claim 2 wherein the device is adapted for delivery of active agent to the omentum.

7. The device of claim 5 or 6 wherein the delivery device is adapted for delivery through a cannula.

8. The device of claim 1, wherein the active agent is stable in the presence of elevated temperature or organic solvents.

9. The device of claim 1, 5 or 6 wherein the active agent is selected from the group consisting of antibodies, enzymes, trophic factors, growth factors, hormones and biological response modifiers.

10. The device of claim 1, 5 or 6 wherein the active agent is an analgesic or pain-reducing substance.

11. The device of claim 9, wherein the active agent is a peptide or protein.

12. The device of claim 11 wherein the active agent is a cytokine or lymphokine.

13. The device of claim 1, wherein the active agent is an immunogen.

14. The device of claim 1, wherein the active agent is prophylactic for use as a vaccine.

15. The device of claim 1, wherein the active agent comprises an antigen and an adjuvant.

16. The device of claim 1, wherein the biomaterial further comprises one or more delivery enhancing agents selected from the group consisting of polyethylene oxide (PEO), heparin, albumin, tissue growth factors, angiogenic growth factors, surfactants, anti-oxidants, anti-inflammatory agents, and anti-rejection medications.

17. The device of claim 16, wherein the angiogenic growth factor is selected from the group consisting of basic fibroblast growth factor, acidic fibroblast growth factor, vascular endothelial growth factor, platelet derived endothelial cell growth factor bb, angiopoietin-1, transforming growth factor beta, transforming growth factor alpha, hepatocyte growth factor, tumor necrosis factor-alpha, angiogenin, interleukin-8, hypoxia inducible factor-i, angiotensin-converting enzyme inhibitor quinaprilat, angiotropin, thrombospondin, lactic acid, insulin, and growth hormone.

18. The device of claim 16, wherein the anti-inflammatory agent is selected from the group consisting of cortisone and ACTH, dexamethasone, cortisol, interleukin-1 and its receptor antagonists, and antibodies to TGF-beta, to interleukin-1 (IL-1), and to interferon-gamma.

19. The device of claim 1, wherein the device is adapted for delivery of active agent at a dose rate from about 0.001 to about 200 micrograms/hr.

20. The device of claim 1, wherein the device is adapted for delivery of active agent at a volume rate of from about 0.01 microliters/day to about 2 ml/day.

21. The device of claim 1, where the back surface of the biomaterial further comprises a substantially resilient substrate material capable of substantially maintaining the shape of the biomaterial.

22. The device of claim 1, wherein the molecular weight cutoff of the membrane is between about 50-2000 kD.

23. The device of claim 1 wherein the molecular weight cutoff of the membrane is above about 100 kD.

24. The device of claim 1 wherein the core comprises a biocompatible matrix formed from a hydrogel.

25. The device of claim 24, where the hydrogel is impregnated with pharmaceuticals.

26. The device of claim 1 wherein the jacket is selected from the group consisting of polyacrylonitrile-polyvinylchloride, polyacrylonitrile, polymethylmethacrylate, polyvinyldifluoride, polyolefins, polysulfones and celluloses.

27. The device of claim 26 wherein the jacket further comprises a hydrophilic or hydrophobic additive.

28. The device of claim 1, where the biomaterial is a tissue matrix structure.

29. The device of claim 28, where the tissue matrix structure includes mammalian cells.

30. The device of claim 29 wherein the cells are allogeneic or syngeneic upon implantation.

31. The device of claim 29 wherein the cells are selected from the group consisting of insulin-producing cells, adrenal chromaffin cells, antibody-secreting cells, fibroblasts, astrocytes, Beta cell lines, and Chinese hamster ovary cells.

32. The device of claim 29 wherein the cells are insulin-producing cells.

33. The device of claim 29 wherein the cells secrete antibodies.

34. The device of claim 29 wherein all of the cells are disposed at a distance no greater than about 800 μm from the front face of the device.

35. The device of claim 29 wherein the delivery device further comprises a core comprising a volume in excess of 1

μl and at least about $10^4$ living cells dispersed in a biocompatible hydrogel matrix, the cells being capable of secreting a active agent or of providing a metabolic or immunologic function.

36. The device of claim 29, wherein the reservoir contains nutrient-rich material and is adapted to delivering the nutrient-rich material to the cells.

37. The device of claim 29 wherein the cells are aggregated into a diffusional aggregate form adapted for increased packing per unit volume.

* * * * *